(12) United States Patent
Li et al.

(10) Patent No.: US 11,369,343 B2
(45) Date of Patent: *Jun. 28, 2022

(54) ULTRASOUND IMAGING BY NONLINEAR LOCALIZATION

(71) Applicant: The Board of Trustees of the Leland Stanford Junior University, Stanford, CA (US)

(72) Inventors: Yilei Li, Palo Alto, CA (US); Steven Chu, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 67 days.

This patent is subject to a terminal disclaimer.

(21) Appl. No.: 16/725,970

(22) Filed: Dec. 23, 2019

(65) Prior Publication Data
US 2020/0237339 A1  Jul. 30, 2020

Related U.S. Application Data

(63) Continuation of application No. 15/990,530, filed on May 25, 2018, now Pat. No. 10,555,721.
(Continued)

(51) Int. Cl.
*A61B 8/14* (2006.01)
*A61B 8/06* (2006.01)
(Continued)

(52) U.S. Cl.
CPC .................. *A61B 8/14* (2013.01); *A61B 8/06* (2013.01); *A61B 8/4477* (2013.01);
(Continued)

(58) Field of Classification Search
CPC ........... A61B 8/06; A61B 8/14; A61B 8/4477; A61B 8/4494; A61B 8/481; A61B 8/488;
(Continued)

(56) References Cited

U.S. PATENT DOCUMENTS 3,987,673 A * 10/1976 Hansen .................... A61B 8/06
73/861.25
5,601,086 A * 2/1997 Pretlow, III ........... A61B 8/481
600/458
(Continued)

FOREIGN PATENT DOCUMENTS

| CN | 101129268 A | 2/2008 |
| CN | 103261909 A | 8/2013 |
| WO | 9940847 A2 | 8/1999 |

OTHER PUBLICATIONS

CN201880042472.X, "Office Action," dated Nov. 12, 2020, 5 pages.

*Primary Examiner* — Colin T. Sakamoto
(74) *Attorney, Agent, or Firm* — Kilpatrick Townsend & Stockton LLP

(57) ABSTRACT

Nonlinear ultrasound imaging systems and methods are disclose. In one aspect, a nonlinear ultrasound imaging system includes a first transducer configured to transmit a first ultrasound signal along a scan line, a second transducer configured to sweep a second ultrasound signal along the scan line such that the first and second ultrasound signals intersect at a plurality of voxels, and a third transducer configured to receive echoes associated with interactions of the first and second ultrasound signals at the plurality of voxels. The nonlinear ultrasound imaging system further includes a processor configured to generate an ultrasound image based on the echoes.

15 Claims, 18 Drawing Sheets

Related U.S. Application Data

(60) Provisional application No. 62/593,519, filed on Dec. 1, 2017, provisional application No. 62/512,048, filed on May 28, 2017.

(51) Int. Cl.

| | | |
|---|---|---|
| *A61B 8/00* | (2006.01) | |
| *A61B 8/08* | (2006.01) | |
| *G01S 7/52* | (2006.01) | |
| *G01S 15/89* | (2006.01) | |

(52) U.S. Cl.
CPC .......... *A61B 8/4488* (2013.01); *A61B 8/5207* (2013.01); *G01S 7/52038* (2013.01); *G01S 15/8913* (2013.01); *G01S 15/8915* (2013.01); *G01S 15/8952* (2013.01); *G01S 15/8995* (2013.01); *A61B 8/4494* (2013.01); *A61B 8/481* (2013.01); *A61B 8/488* (2013.01)

(58) Field of Classification Search
CPC .............. A61B 8/5207; G01S 7/52038; G01S 15/8913; G01S 15/8915; G01S 15/8952; G01S 15/8995
See application file for complete search history.

(56) References Cited

U.S. PATENT DOCUMENTS

| | | | | |
|---|---|---|---|---|
| 5,903,516 | A | * | 5/1999 | Greenleaf ........... G01S 15/8952 367/92 |
| 5,991,239 | A | * | 11/1999 | Fatemi-Booshehri ...................... G10K 15/02 310/320 |
| 2002/0040188 | A1 | * | 4/2002 | Averkiou ............ G01S 7/52095 600/458 |
| 2004/0054284 | A1 | | 3/2004 | Cai et al. |
| 2009/0281422 | A1 | * | 11/2009 | Salama .................... A61B 5/05 600/430 |
| 2011/0301466 | A1 | | 12/2011 | Wang et al. |
| 2012/0095699 | A1 | * | 4/2012 | Angelsen ............ G01S 7/52038 702/33 |
| 2015/0141874 | A1 | * | 5/2015 | Wilson ..................... A61N 7/02 601/3 |
| 2015/0289846 | A1 | * | 10/2015 | Park ..................... A61B 8/5207 600/447 |
| 2016/0339273 | A1 | * | 11/2016 | Al Mayiah ............... A61N 7/02 |

* cited by examiner

ULTRASOUND IMAGING BY NONLINEAR LOCALIZATION

RELATED APPLICATIONS

This application is a continuation of U.S. patent application Ser. No. 15/990,530, filed May 25, 2018, entitled "ULTRASOUND IMAGING BY NONLINEAR LOCALIZATION," which claims the benefit of priority of U.S. Provisional Patent Application No. 62/512,048, filed May 28, 2017, entitled "SPECKLE-FREE ULTRASOUND IMAGING BY NONLINEAR LOCALIZATION," and also claims the benefit of priority of U.S. Provisional Patent Application No. 62/593,519, filed Dec. 1, 2017, entitled "NONLINEAR CONTRAST ULTRASOUND IMAGING." The contents of each of these priority applications are hereby incorporated by reference herein in their entireties and for all purposes.

FEDERAL SUPPORT STATEMENT

This invention was made with government support under contract GM128089 awarded by the National Institutes of Health. The government has certain rights in the invention.

BACKGROUND

Technological Field

The disclosed technology relates to nonlinear ultrasound imaging.

Description of the Related Technology

Ultrasound imaging is an increasingly important tool for diagnostic imaging with many desirable characteristics. Ultrasound imaging is used to image internal structures of a patient, such as muscles, blood vessels, organs, and to diagnose (or exclude) various diseases and conditions. Ultrasound imaging is widely used on pregnant women to monitor healthy growth of fetuses in utero.

Ultrasounds are sound waves with frequencies above the audible range of humans, which generally extends up to about 20 kHz. Ultrasonic images are generated by sending pulses of ultrasound into tissues of a patient (or other object being imaged) using an ultrasonic emitter or transducer. The ultrasound reflects or echoes off of the tissue. An ultrasound receiver or transducer receives the echoes and processes them into an image that provides useful information about the patient's tissues. The most common type of ultrasound image is the B-mode image. A B-mode image illustrates the acoustic impedance of a two-dimensional cross-section of the tissue being imaged. The acoustic impedance of tissue is a linear elastic property given by the product of the density and velocity of sound in the tissue.

Ultrasound imaging has several advantages over other forms of medical imaging as it is relatively fast, provides real-time imaging, has a low cost, and does not expose patients to ionizing radiation such as would be the case with x-ray diagnostics. However, ultrasound imaging methods and systems can suffer from the presence of significant speckle noise (e.g., significant and widespread background noise in ultrasound images due to back-scattering of sound by the tissue being imaged), and useful resolution of ultrasound imaging in clinical practice can be degraded.

SUMMARY OF CERTAIN INVENTIVE ASPECTS

The innovations described in the claims each have several aspects, no single one of which is solely responsible for its desirable attributes. Without limiting the scope of the claims, some prominent features of this disclosure will now be briefly described.

One aspect of this disclosure is a method of nonlinear ultrasound imaging. The method includes transmitting a first ultrasound signal centered at a first frequency and transmitting a second ultrasound signal centered at a second frequency, where transmitting the second ultrasound signal includes sweeping the second ultrasound signal in a direction such that the second ultrasound signal intersects with the first ultrasound signal at a plurality of voxels along a scan line as the first ultrasound signal propagates along the scan line and where the second frequency is different than the first frequency. The method further includes processing echoes associated with interaction of the first ultrasound signal and the second ultrasound signal in the voxels along the scan line and generating an ultrasound image based on the processing.

The method can further include frequency modulating at least one of the first and second frequencies among discrete frequencies during the sweeping.

In the method, processing the echoes may further include differentiating two echoes of the echoes based at least partly on the modulation of at least one of the first and second frequencies, where the two echoes are associated with adjacent voxels of the voxels.

In the method, processing the echoes may further include frequency compounding.

In the method, processing the echoes may further include spatial compounding.

In the method, a phased array of ultrasound transducers may perform the sweeping of the second ultrasound signal.

The method can further include visually displaying a B-mode image that represents the ultrasound image.

In the method, a feature having a dimension of approximately 1 millimeter may be identifiable in the B-mode image displayed in the method.

In the method, a frequency of an echo associated with a voxel of the voxels may correspond to a difference between the first frequency of the first ultrasound signal and the second frequency of the second ultrasound signal in the voxel.

In the method, the first frequency of the first ultrasound signal and the second frequency of the second ultrasound signal may differ by at least 500 kilohertz.

In the method, generating the ultrasound image may include generating ultrasound images in real-time at a framerate of at least 10 Hertz.

Another aspect of this disclosure is an ultrasound imaging system. The system includes a first transducer configured to transmit a first ultrasound signal centered at a first frequency along a scan line and a second transducer configured to sweep a second ultrasound signal centered at a second frequency along a direction such that the second ultrasound signal intersects with the first ultrasound signal at a plurality of voxels along the scan line as the first ultrasound signal propagates along the scan line, where the first and second frequencies are different. The system further includes a third transducer configured to receive an echo associated with interaction of the first ultrasound signal and the second ultrasound signal in a voxel of the voxels, the echo centered at a third frequency that is based on the first frequency of the first ultrasound signal and the second frequency of the second ultrasound signal and a processing circuit configured to generate an ultrasound image based on the echo.

In the ultrasound imaging system, the second transducer may be configured to frequency modulate the second ultrasound signal among discrete frequencies.

In the ultrasound imaging system, the processing circuit may be configured to differentiate echoes associated with interaction of the first ultrasound signal and the second ultrasound signal from adjacent voxels of the voxels based on frequencies of the echoes associated with the adjacent voxels.

In the ultrasound imaging system, the first transducer may include a linear phased array of ultrasound transducers.

In the ultrasound imaging system, the first transducer may be configured to frequency modulate the first ultrasound signal among discrete frequencies.

In the ultrasound imaging system, the processing circuit may be configured to perform frequency compounding.

The ultrasound imaging system may also include a display configured to visually present the ultrasound image.

Another aspect of this disclosure is an ultrasound transducer head. The ultrasound transducer head includes a first phased transducer array configured to transmit a first ultrasound signal centered at a first frequency, a second phased transducer array configured to transmit a second ultrasound signal centered at a second frequency and non-collinearly with the first ultrasound signal, the first and second frequencies being different, and a third transducer array configured to detect an echo having a frequency that is associated with interaction of the first ultrasound signal and the second ultrasound signal. In the ultrasound transducer head, the first phased traducer array, the second phased transducer array, and the third phased transducer array may be included on a common transducer head.

In the ultrasound transducer head, the first phased transducer may be configured to sweep the first ultrasound signal in direction, the second phased transducer array may be configured to sweep the second ultrasound signal in direction and to modulate the second frequency of the second ultrasound signal among discrete frequencies, and the third phased transducer array may be configured to focus at the intersection of the first and second ultrasound signals.

For purposes of summarizing the disclosure, certain aspects, advantages and novel features of the innovations have been described herein. It is to be understood that not necessarily all such advantages may be achieved in accordance with any particular embodiment. Thus, the innovations may be embodied or carried out in a manner that achieves or optimizes one advantage or group of advantages as taught herein without necessarily achieving other advantages as may be taught or suggested herein.

BRIEF DESCRIPTION OF THE DRAWINGS

Embodiments of this disclosure will now be described, by way of non-limiting example, with reference to the accompanying drawings.

DETAILED DESCRIPTION

Figure 1A:
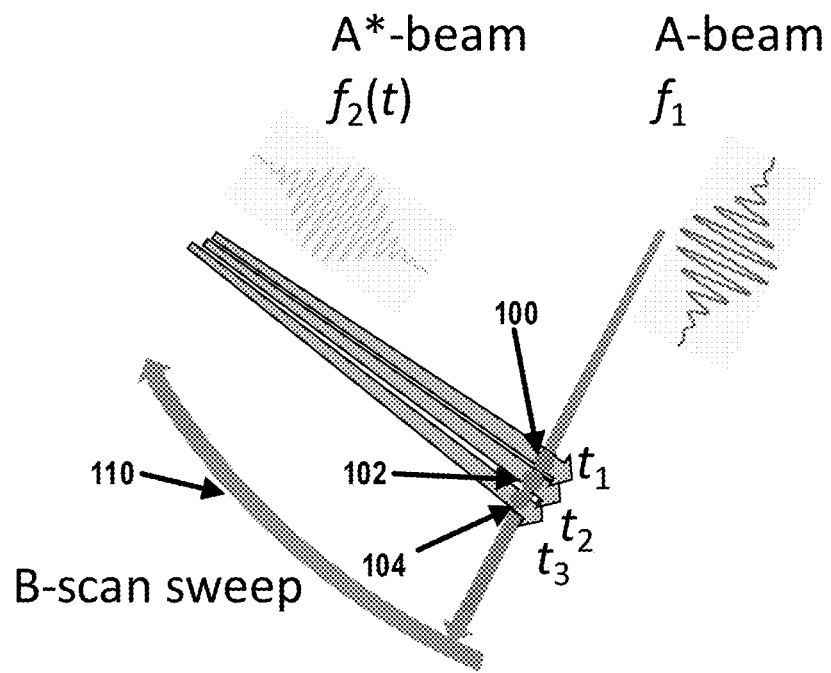
FIG. 1A illustrates intersecting ultrasonic pulses for an A-scan utilizing intersecting beams and also illustrates how a B-scan image can be formed with a sweep of the intersecting beams according to an embodiment of the disclosed technology.

The following detailed description of certain embodiments presents various descriptions of specific embodiments. However, the innovations described herein can be embodied in a multitude of different ways, for example, as defined and covered by the claims. In this description, reference is made to the drawings where like reference numerals can indicate identical or functionally similar elements. It will be understood that elements illustrated in the figures are not necessarily drawn to scale. Moreover, it will be understood that certain embodiments can include more elements than illustrated in a drawing and/or a subset of the elements illustrated in a drawing. Further, some embodiments can incorporate any suitable combination of features from two or more drawings. The headings provided herein are for convenience only and do not necessarily affect the scope or meaning of the claims.

I. NONLINEAR ULTRASONIC IMAGING SYSTEMS AND METHODS

The technology disclosed herein uses acoustic frequency mixing, where sound at two frequencies interacts in a nonlinear medium to generate a third frequency. In certain embodiments, difference-frequency generation is used. Sum-frequency and/or higher-order nonlinear mixing can alternatively or additionally be used. For pulses with frequencies centered at $f_1$ and $f_2$, corresponding to wavelengths of $\lambda_1$ and $\lambda_2$, the nonlinear sound at the difference frequency has a central frequency $f_{NL}=|f_1-f_2|$ and a central wavelength $\lambda_{NL}$ satisfying $1/\lambda_{NL}=|1/\lambda_1-1/\lambda_2|$. The two pulses propagate non-collinearly, so that the nonlinear signal is only generated when the two pulses intersect in space and time, hence interrogating nonlinear acoustic response of the intersection voxel. The optimized resolution may be achieved when the two pulses intersect with an angle of approximately 90 degrees. Additionally, $\lambda_{NL}$ can be tuned by adjusting $\lambda_1$ and/or $\lambda_2$, allowing for further reduction in speckle by frequency compounding.

In at least some embodiments, the excitation frequencies are associated with ultrasound pulses that propagate non-collinearly, so that the nonlinear signal is only generated when the two pulses intersect. A coordinated sweep of the interacting pulses of the excitation frequencies allows for rapid imaging. Moreover, the nonlinear signal $\lambda_{NL}$ can be tuned by adjusting the excitation signals at wavelengths of $\lambda_1$ and/or $\lambda_2$, allowing for further reducing in speckle by frequency or spectral compounding.

One ultrasound imaging mode is the B-mode, where the brightness of a pixel represents the echogenicity, or the echo strength, of the corresponding voxel inside the tissue. The B-mode sound echo is created by changes in the acoustic impedance, given by the product of the density and velocity of sound. Tissue harmonic imaging can be used to improve the quality of B-mode images, making use of the harmonics generated as the fundamental wave propagates into the tissue. Since the harmonics are produced away from the surface, the reverberation effect is significantly reduced. Another advantage of tissue harmonic image is that the shorter wavelength of the harmonics results in better resolution than the fundamental (e.g., excitation) wavelength. While harmonic generation originates from the nonlinearity of the medium, the brightness of a pixel in the harmonic image is produced by the linearly back-scattered sound. As a result, the contrast of the harmonic images still represents the linear contrast.

The nonlinear frequency mixing is caused by a second-order change in density with respect to pressure. Hence, the nonlinear image is expected to have a different contrast than the linear image. Further, the contrast for certain anatomic features can be drastically enhanced.

As discussed above, ultrasound imaging is becoming an increasingly important tool for diagnostic imaging. Ultrasound imaging has many desirable characteristics, such as relatively fast, real-time imaging, low cost, and no exposure to ionizing radiation such as would be the case with x-ray diagnostics. However, ultrasound imaging can suffer from the presence of significant speckle noise (e.g., significant and widespread background noise in ultrasound images due to back-scattering of sound by the tissue being imaged). In clinical and other settings, the useful resolution of such ultrasound images can be degraded by the speckle noise.

Speckle noise can be the result of coherent back-scattering of sound by the distribution of scatterers within each scattering voxel. A voxel is the individual unit of spatial volume being imaged. In each voxel, suppose we have scattering amplitudes $A_1(\vec{x}_1)$, $A_2(\vec{x}_2)$, $A_3(\vec{x}_3)$, .... If these amplitudes interfere constructively or destructively, the scattered signal $|A_1(\vec{x}_1)+A_2(\vec{x}_2)+A_3(\vec{x}_3)+\ldots|^2$ can be either more or less than the sum of the scattering intensities of each of the scatterers, $|A_1(\vec{x}_1)|^2+|A_2(\vec{x}_2)|^2+|A_3(\vec{x}_3)|^2+\ldots$, thus producing speckle.

There are several approaches for speckle reduction. One method is to average over N independent speckle images, which can reduce the speckle by $\sqrt{N}$. The multiple images can be obtained by using different portions of an ultrasound array. In a linear array of total aperture length L, the resolution at any given depth z is approximately proportional to L/z. If the aperture is broken up into N sub-segments for the purposes of speckle reduction, the spatial aperture of each view is decreased by N and the resolution becomes (L/N)/z. Thus, this method of speckle reduction sacrifices both image acquisition time and spatial resolution. There are also post data-collection image processing algorithms. However, due to the randomness and high density of the speckle pattern, post data-collection algorithms in general have not been able to recover all the lost information hidden in the speckle image.

A system and a method for generating ultrasound images and contrast ultrasound images with reduced speckle is provided. The reduction of speckle can be achieved by detecting nonlinear ultrasound radiation generated from a localized spatial volume, such as a voxel, defined by the intersection of multiple excitation ultrasound pulses. The nonlinear ultrasound radiation can be generated at a difference frequency equal to a difference between the excitation ultrasound pulses. While various embodiments disclosed herein are described in connection with difference frequency signals, sum-frequency and/or higher-order nonlinear signals could be used instead of or in addition to difference frequency signals. The localized spatial volume is scanned by spatial scanning of the excitation ultrasound pulses to form the full image. In other words, the excitation ultrasound pulses are scanned over a desired area or volume to image a series of voxels and build up a full image of the area or volume. In at least some embodiments, increased wavelengths of the difference frequency ultrasound radiation reduce speckle.

This approach reduces speckle while preserving spatial resolution. Applications of the disclosed technology include, but are not limited to, medical diagnostic ultrasound imaging.

New methods and devices for ultrasound imaging with significantly reduced speckle level are disclosed herein. The methods and devices utilize acoustic difference-frequency generation in which sound at two excitation frequencies interacts in a nonlinear medium to generate an ultrasound return signal at a third frequency, which is equal to the difference of those two frequencies. Consider the case of two excitation frequencies centered at $f_1$ and $f_2$, corresponding to wavelengths of $\lambda_1$ and $\lambda_2$, respectively. The nonlinear difference-frequency return signal has a central wavelength $\lambda_{NL}$ satisfying $1/\lambda_{NL}=1/\lambda_1-1/\lambda_2$. From this relation, one can see that $\lambda_{NL}$ is longer than the wavelengths $\lambda_1$ and $\lambda_2$. Advantageously, one can choose $\lambda_1$ and $\lambda_2$ and the imaging configuration, such that the wavelength of the nonlinear signal $\lambda_{NL}$ is significantly greater than the image voxel's dimension. As a result, one may expect that the generated nonlinear amplitudes in each voxel have essentially the same phase and constructively interfere. However, due to the interference fringes within the voxel, speckle is not completely eliminated, but there can be a finite suppression in speckle. Speckle suppression can be further improved by compounding images corresponding to a number of difference-frequencies.

II. AN EXAMPLE EMBODIMENT OF NONLINEAR ULTRASOUND IMAGING

Figure 3A:
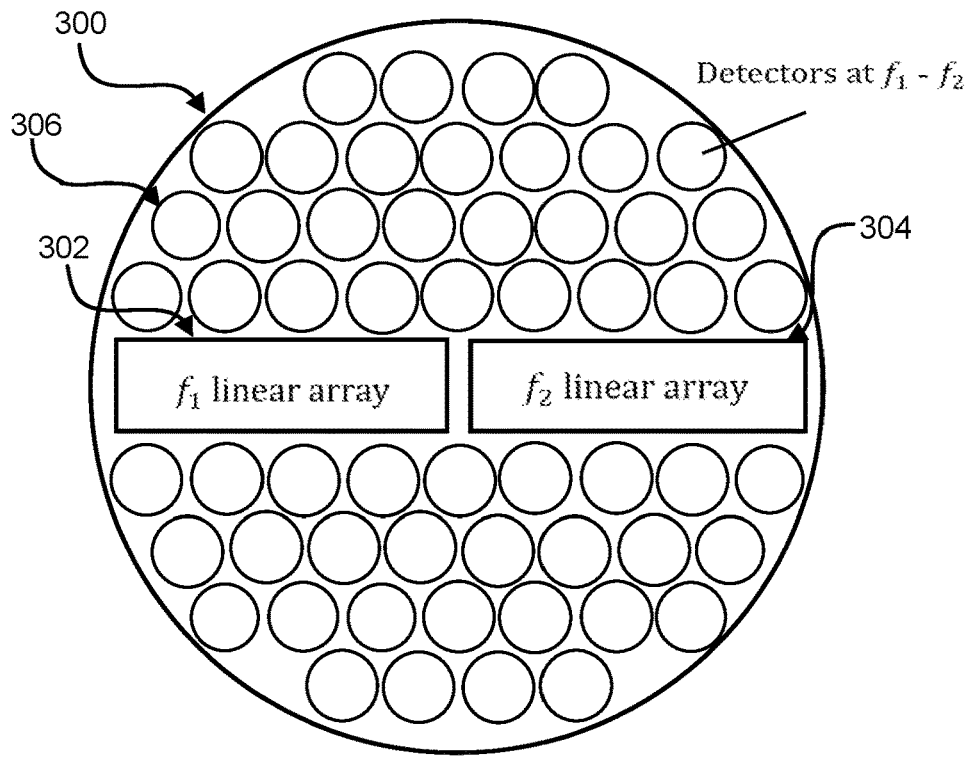
FIG. 3A illustrates an ultrasonic transducer head that includes two linear arrays that can transmit the intersecting beams of FIG. 1A and an array of transducer elements that can receive ultrasonic return signals according to an embodiment of the disclosed technology.

In an example embodiment, an imaging voxel is defined by two excitation beams, such as the A and A* beams of FIG. 1A generated by first and second transducers such as transducer arrays 302 and 304 of FIG. 3A, intersecting in both space and time. The A-beam can have a frequency $f_1$ and the A*-beam can have a frequency $f_2(t)$. In each line scan, the A-scan transmitter emits an acoustic Fourier-transform limited Gaussian pulse of duration $\lambda t$ $$g(t) = \frac{1}{(2\pi\sigma^2)^{\frac{1}{2}}} \exp\left[-\frac{t^2}{2\sigma^2}\right], \quad (1)$$

$$\Delta t \Delta \omega = 1,$$

where $\Delta\omega=2\pi\Delta f$ and $\Delta t$ are the 1 σ widths of the Gaussian Fourier transforms, respectively. The full-width at half maximum of the pulse $\Delta t_{FWHM}=2.35\,\Delta t$. The A*-beam can be swept in direction using a phased array, so that its focus continually intersects the A-beam as the A-beam penetrates into tissue.

FIG. 1A illustrates an A-beam intersecting a sweeping A*-beam at different points in time and space. An angle between the A-beam and the A*-beam can be approximately 90 degrees. The angle between the A-beam and the A*-beam can be in a range from about 40 degrees to 140 degrees in certain applications. As illustrated in FIG. 1A, the A*-beam can be swept in direction such that it intersects the A-beam at voxels 100, 102, and 104. Detection of an echo at a difference frequency at different time delays corresponds to different z-positions along a scan line of the A-scan. A B-scan image can be formed by the coordinated sweep of the A- and A*-beams. A processing circuit of the ultrasound imaging system can image the nonlinear response from the voxels 100, 102, and 104. After the A* beam has scanned along the length of the A-beam (within the desired depths of the object being imaged), the A beam can be stepped to another direction such as along the B-scan sweep 110 such that additional voxels (e.g., voxels adjacent to voxels 100, 102, and 104) can be imaged. In this manner, the system can obtain a B-scan of the object being imaged.

In some other embodiments, the A-beam may be scanned along the A* beam, and the A*-beam may be sweep across the B-scan sweep 110. In still other embodiments, the A-beam and the A*-beam may be swept independently, in unison, or in any other manner in order to move the actively imaged voxel around within the object being imaged in any desired manner.

Figure 1B:
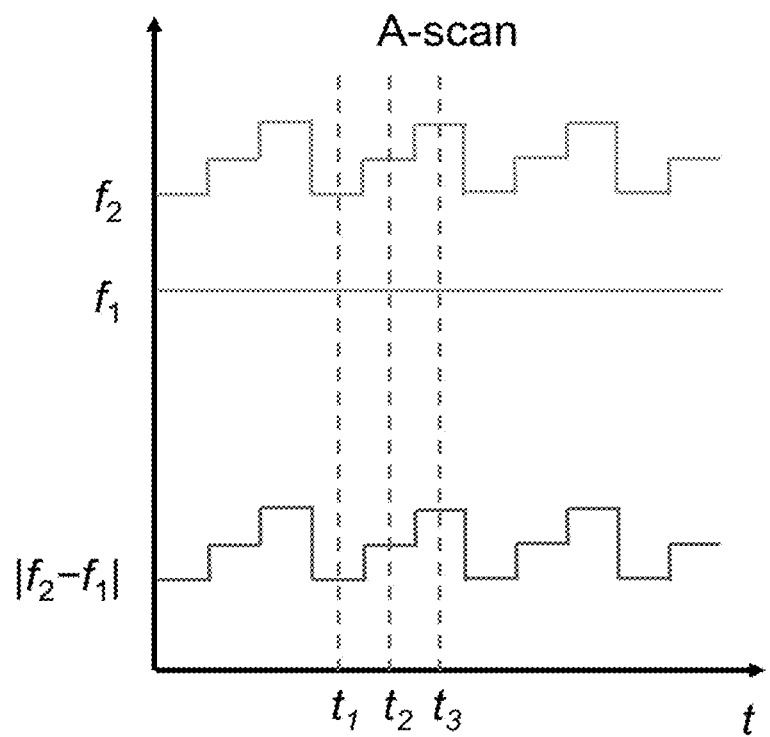
FIG. 1B illustrates frequencies of the ultrasonic pulses of the intersecting beams of FIG. 1A and of echoes as a function of time according to an embodiment of the disclosed technology.

To avoid coherent interference of the nonlinear signal generated in adjacent voxels, the frequency $f_2(t)$ of the A*-beam may vary over time. In particular, the frequency $f_2(t)$ of the A*-beam may be switched between two or more discrete frequencies as it is swept in direction. FIG. 1B illustrates one example of how the frequency $f_2(t)$ of the A*-beam may be switched between three center frequencies. Shifting the frequency of the A*-beam in this manner can allow digital filtering of the different difference-frequencies, such that adjacent voxels can be easily distinguished. As an example, voxel 100 may be excited with the A-beam at a first sub-frequency of $f_2$ and the A-beam at frequency $f_1$, while voxels 102 and 104 may excited with the A*-beam modulated to a second sub-frequency of $f_2$. The A*-beam may excite voxels 100, 102, and 104 in this manner by emitting a series of pulses at different center frequencies, as illustrated in FIG. 1B, each of which is timed to intersect with a corresponding pulse from the A-beam at a desired depth (e.g., at a desired voxel) within the object being imaged. With this arrangement, voxels 100, 102, and 104 respectively generate nonlinear return signals having frequencies at the difference between $f_1$ and either the first, second, or third sub-frequency of $f_2$. These return signals can be distinguished by any desired filtering techniques. The switching of the center frequencies of the A*-beam may be achieved by programming the output of an arbitrary waveform generator.

FIG. 1B shows center frequencies of the A-beam, A*-beam, and their difference-frequency as a function of time at the location of their intersection. As shown in FIG. 1B, the A-beam can be constant and centered at $f_1$. The A*-beam can switch its center frequency among three frequencies as shown in FIG. 1B. The A*-beam can be modulated to have two or more frequencies. Alternatively, the A-beam can be modulated in frequency and the A*-beam can be modulated in frequency to generate a different difference-frequencies in adjacent voxels along a scan line.

The technique of FIGS. 1A and 1B may enable nonlinear ultrasound systems to obtain ultrasound images in real-time at rates comparable to linear ultrasound systems. In particular, the nonlinear ultrasound systems disclosed herein may be able to obtain ultrasound images at a frame rate of at least 1 Hz, at least 5 Hz, at least 10 Hz, at least 20 Hz, or at least 30 Hz. Additionally, the systems may capture nonlinear ultrasound images of at least 100 by 100 pixels, at least 200 by 200 pixels, or at least 400 by 400 pixels and may capture such images at a real-time frame rates such as at least 1 Hz, at least 5 Hz, at least 10 Hz, at least 20 Hz, or at least 30 Hz. The relatively high rate of imaging may be enabled by the rapid sweep of the A* beam along the scan line. In particular, the imaging rate of linear ultrasound systems may be limited by the round-trip propagation time of ultrasound pulses along a given scan line of the A-beam. To build an entire image, the A-beam may have to sweep along the B-scan sweep line (such as line 110 of FIG. 1A) and the A-beam may have to linger at each scan line for the round-trip propagation time. With the present nonlinear system, the A*-beam may sweep along the A-beam over approximately the round-trip propagation time. Thus, the A-beam may be able to sweep along the B-scan sweep line 110 at approximately the same rate in linear and nonlinear imaging modes and the nonlinear ultrasound imaging systems disclosed herein can provide a relatively high frame rate B-mode imaging.

The difference frequency sound can be detected by a third transducer, such as elements 306 of transducer head 300 of FIG. 3A, which is sensitive to the difference frequencies. An analog filter can be used to attenuate background away from the difference frequency bands. After amplification of the nonlinear signal, the voltage signal can be digitized. To determine the signal from a voxel at depth z along the line scan, the digitized signal can be analyzed in a time window centered at the corresponding time delay, which can be expressed as $t=(z+z')/c$, where $z'$ is the distance from the imaging voxel to the detector and c is the speed of sound. The time window has a duration given approximately by the voxel depth divided by the speed of sound.

Further filtering in the frequency domain can be performed by digital Fourier transformation of the time domain signal and then selecting the frequency band in the frequency domain as discussed above. The nonlinear signal can be obtained by integrating the resulting difference frequency intensity.

With the methods corresponding to FIGS. 1A and 1B, the speed of data acquisition is not compromised compared to a conventional scan since the A-scan time is still determined by the traveling time of the acoustic pulse through the depth of the scan range. The A* transducer can emitting a continuous stream of ultrasound pulses during the transit time of the A-scan.

Figure 1C:
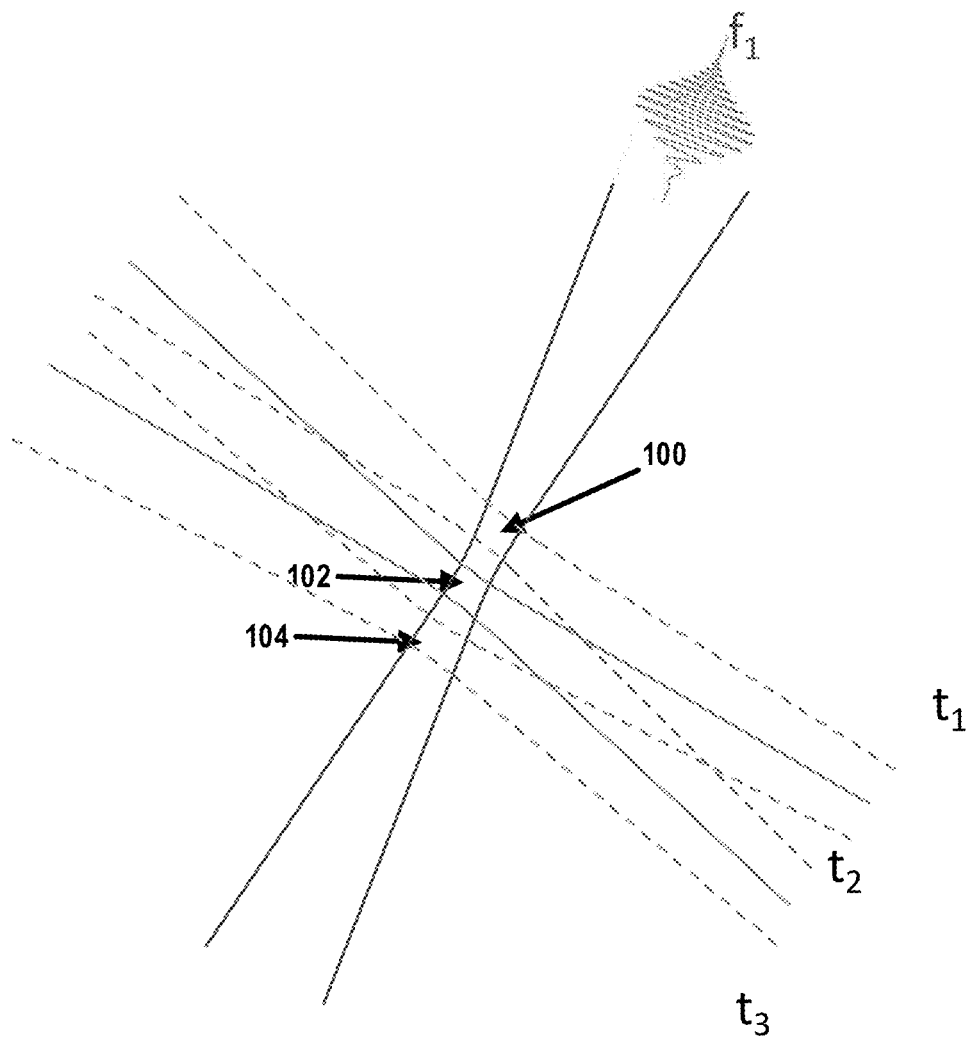
FIG. 1C illustrates ultrasonic pulses intersection at a plurality of voxels according to an embodiment of the disclosed technology.

FIG. 1C illustrates ultrasonic pulses intersection at a plurality of voxels according to an embodiment of the disclosed technology. During a single pulse of a first transducer transmitting an ultrasound signal at frequency $f_1$, a second transducer transmitting an ultrasound signal at frequency $f_2$ can be swept in position so that it intersects with the first ultrasound signal at time resolved points $t_1$, $t_2$, $t_3$, etc. As shown in FIG. 1C, to optimize the nonlinear signal and minimize voxel size, focused phased arrays can be used to change the focal spots at $f_1$ and $f_2$ for each successive pulse of the second ultrasound signal. FIG. 1C also illustrates voxels 100, 102, and 104, which may be various localized spatial volumes within a larger object that is being imaged by the system.

Figure 1D:
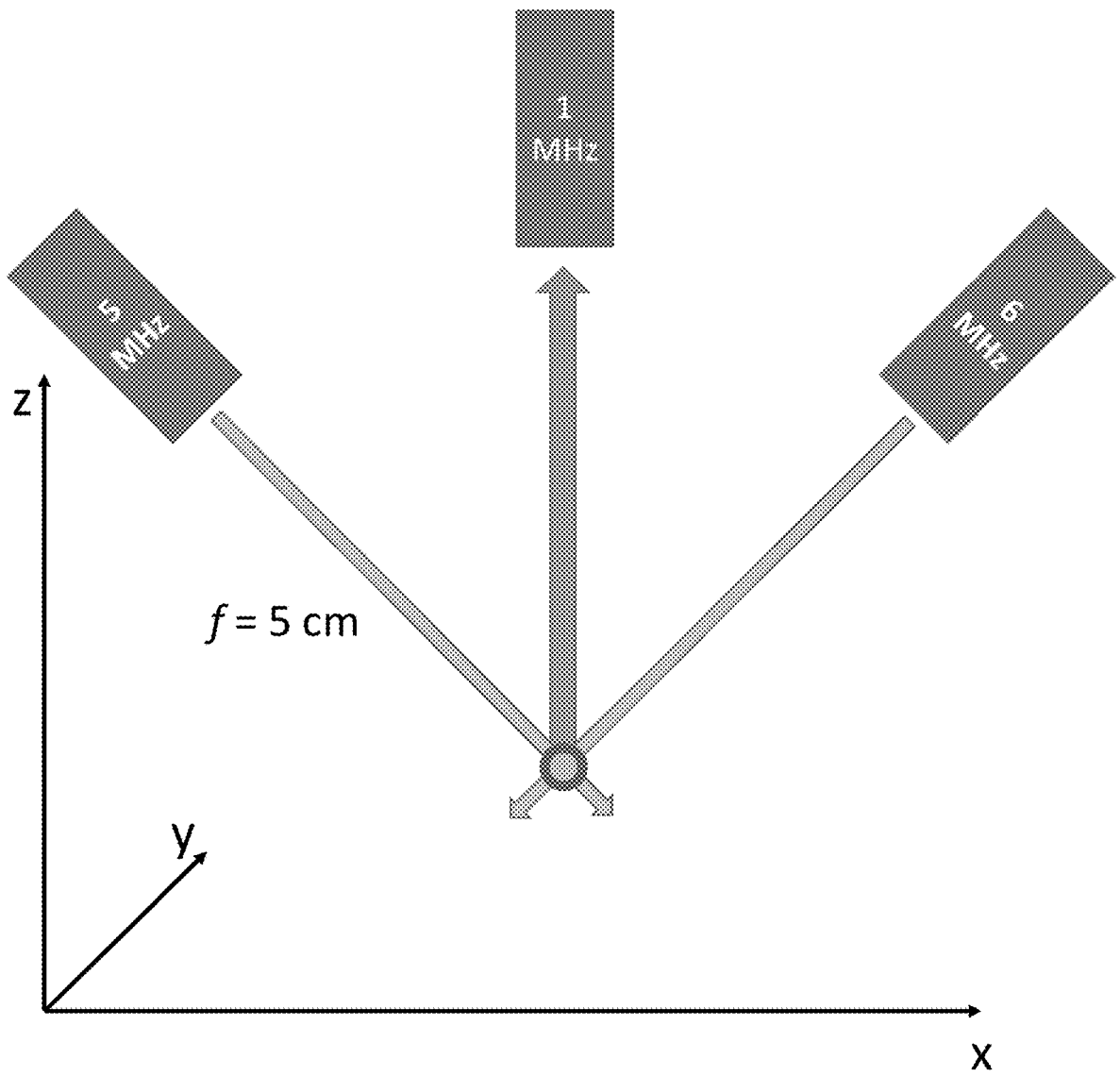
FIG. 1D illustrates transducers arranged to transmit ultrasound signals having different frequencies and another transducer arranged to receive echoes associated with interaction of the ultrasound signals from the transducers according to an embodiment of the disclosed technology.

FIG. 1D illustrates transducers arranged to transmit ultrasound signals having different frequencies and another transducer arranged to receive echoes associated with interaction of the ultrasound signals from the transducers according to an embodiment of the disclosed technology. As shown in FIG. 1D, a first transducer is arranged to transmit an ultrasound signal having a frequency 5 MHz and a second transducer is configured to transmit an ultrasound signal having a frequency of 6 MHz. A third transducer is arranged to detect a difference-frequency signal having a frequency of 1 MHz associating with interaction of the ultrasound signals from the first and second transducers in a voxel at which they intersect in space and time.

III. FREQUENCY COMPOUNDING IN NONLINEAR ULTRASOUND IMAGING

Frequency compounding can be applied to nonlinear contrast imaging to reduce speckle. A refined speckle reduction scheme that involves frequency compounding that may not reduce the frame rate can be applied to nonlinear contrast imaging. As an example, N A-pulses are sent out sequentially during one A-scan for an N-fold frequency compounding. The A-pulses are delayed by one imaging voxel. N trains of A*-pulses are transmitted to intersect with the N A-pulses to generate the difference frequency signal. For the purpose of illustration, let us consider the case for N=3. The three A-pulses are centered at $f_1$. The three A*-pulse trains have center frequencies $f_2$, $f_2'$, and $f_2''$, respectively. Each A* pulse train traces one of the A-pulses, generating difference frequencies centered at $|f_2-f_1|$, $|f_2'-f_1|$, and $|f_2''-f_1|$, respectively.

Table 1 summarizes the nonlinear frequency generation at different imaging depth and time delays. At the receiving end, multiple frequencies are detected as a function of time delay. Digital frequency filtering and receive focusing allows for the separation of the frequencies (and thus different depths). For example, at time $t_0$, the signal detected will be from depth $t_0c$ at frequency $|f_2-f_1|$, from depth $(t_0-\Delta t)c$ at frequency $|f_2'-f_1|$, and from depth $(t_0-2\Delta t)c$ at frequency $|f_2''-f_1|$. At time $t_0+\Delta t$, signal at $|f_2'-f_1|$ from depth $t_0$ c is detected. With this scheme, each voxel is imaged at N difference frequencies in one A scan, and hence the frame rate is maintained. Compounding N nonlinear frequency bands reduces speckle by a factor of $\sqrt{N}$.

TABLE 1

Frequency compounding scheme that may not reduce the frame rate. The rows may correspond to imaging voxels (Δtc is the voxel size) at different depths and the columns correspond to different time delays. The entries in the table may be the nonlinear frequencies emitted from the corresponding imaging voxels and the time delays.

|  | ... $t_0$ | $t_0 + \Delta t$ | $t_0 + 2\Delta t$ | $t_0 + 3\Delta t$ | $t_0 + 4\Delta t$ | ... |
|---|---|---|---|---|---|---|
| $(t_0 - 2\Delta t)c$ | ... $\|f_2'' - f_1\|$ | | | | | |
| $(t_0 - \Delta t)c$ | ... $\|f_2' - f_1\|$ | $\|f_2'' - f_1\|$ | | | | |
| $t_0c$ | $\|f_2 - f_1\|$ | $\|f_2' - f_1\|$ | $\|f_2'' - f_1\|$ | | | |
| $(t_0 + \Delta t)c$ | | $\|f_2 - f_1\|$ | $\|f_2' - f_1\|$ | $\|f_2'' - f_1\|$ | | |
| $(t_0 + 2\Delta t)c$ | | | $\|f_2 - f_1\|$ | $\|f_2' - f_1\|$ | $\|f_2'' - f_1\|$ | |

TABLE 1-continued

Frequency compounding scheme that may not reduce the frame rate. The rows may correspond to imaging voxels ($\Delta t_c$ is the voxel size) at different depths and the columns correspond to different time delays. The entries in the table may be the nonlinear frequencies emitted from the corresponding imaging voxels and the time delays.

| | ... $t_0$ | $t_0 + \Delta t$ | $t_0 + 2\Delta t$ | $t_0 + 3\Delta t$ | $t_0 + 4\Delta t$ | ... |
|---|---|---|---|---|---|---|
| $(t_0 + 3\Delta t)c$ | | | | $|f_2 - f_1|$ | $|f_2' - f_1|$ | ... |
| $(t_0 + 4\Delta t)c$ | | | | | $|f_2 - f_1|$ | ... |

Figure 2:
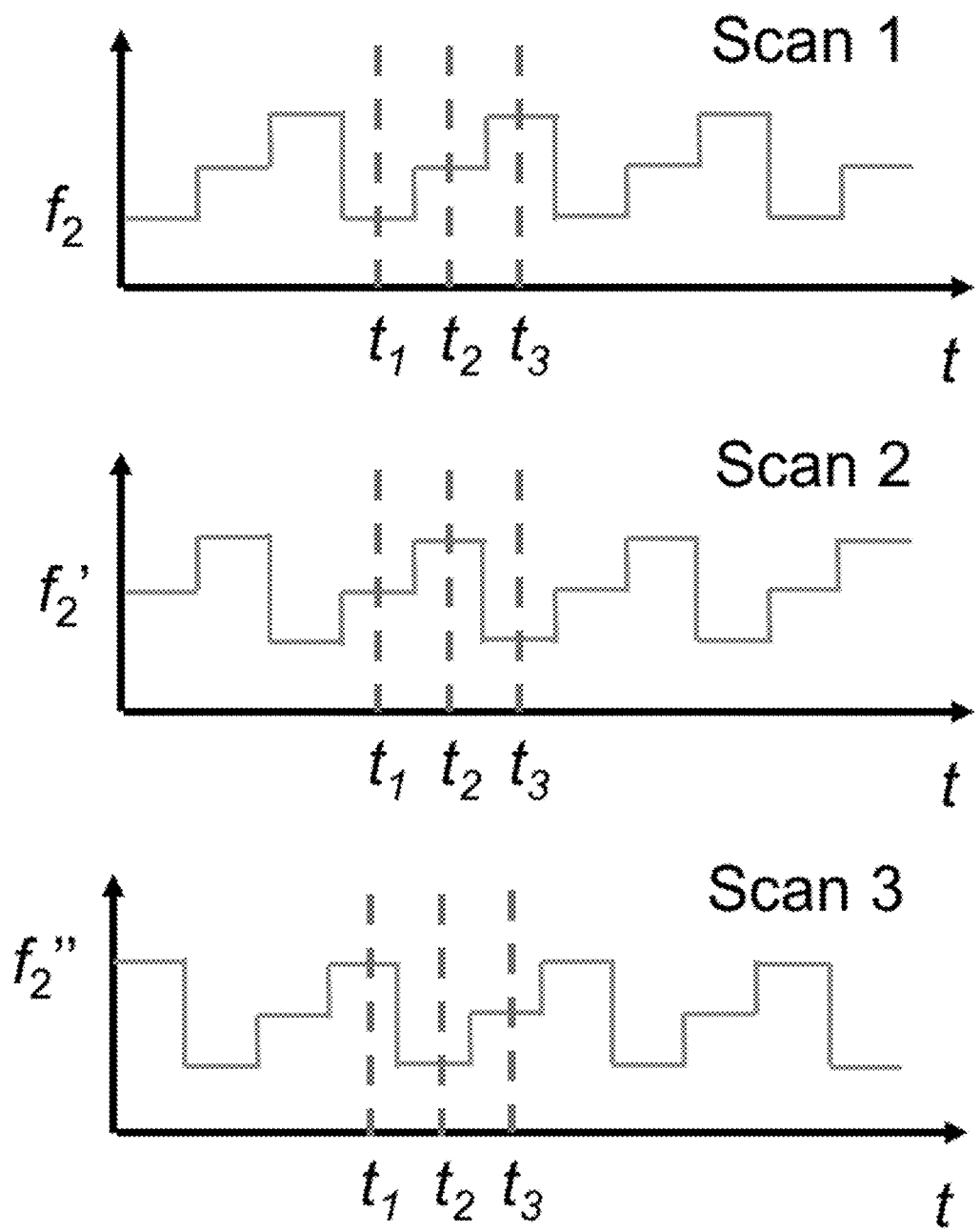
FIG. 2 illustrates graphs of ultrasonic pulses of the one of the beams of FIG. 1A for three scans that can form a basis for frequency compounding according to an embodiment of the disclosed technology.

Graphs illustrating an example of the frequency compounding scheme for N=3 are shown in FIG. 2. To further improve speckle suppression, additional A-scans can be made where the frequency is shifted step-wise in time so that at each depth $z(t_1, f_2)$ along a scan line the frequency $f_2$ is shifted to $f_2'$ and then to $f_2''$ for 3 successive A-scans. Multiple nonlinear bands are then produced at $f_{NL}=|f_2-f_1|$, $|f_2'-f_1|$, $|f_2''-f_1|$, .... The frequency bands in the A*-beam can be separated to allow the nonlinear bands to be distinguished with digital filtering. In other words, each of the frequencies $f_2(t)$, $f_2'(t)$, and $f_2''(t)$ of the A*-beam may be switched between two or more frequencies to facilitate distinguishing echoes from adjacent voxels, for example, as described in connection with FIGS. 1A and 1B. Compounding of these nonlinear frequency bands may further reduce speckle by a factor of $\sqrt{N}$, where N is the number of nonlinear bands.

Figure 8:
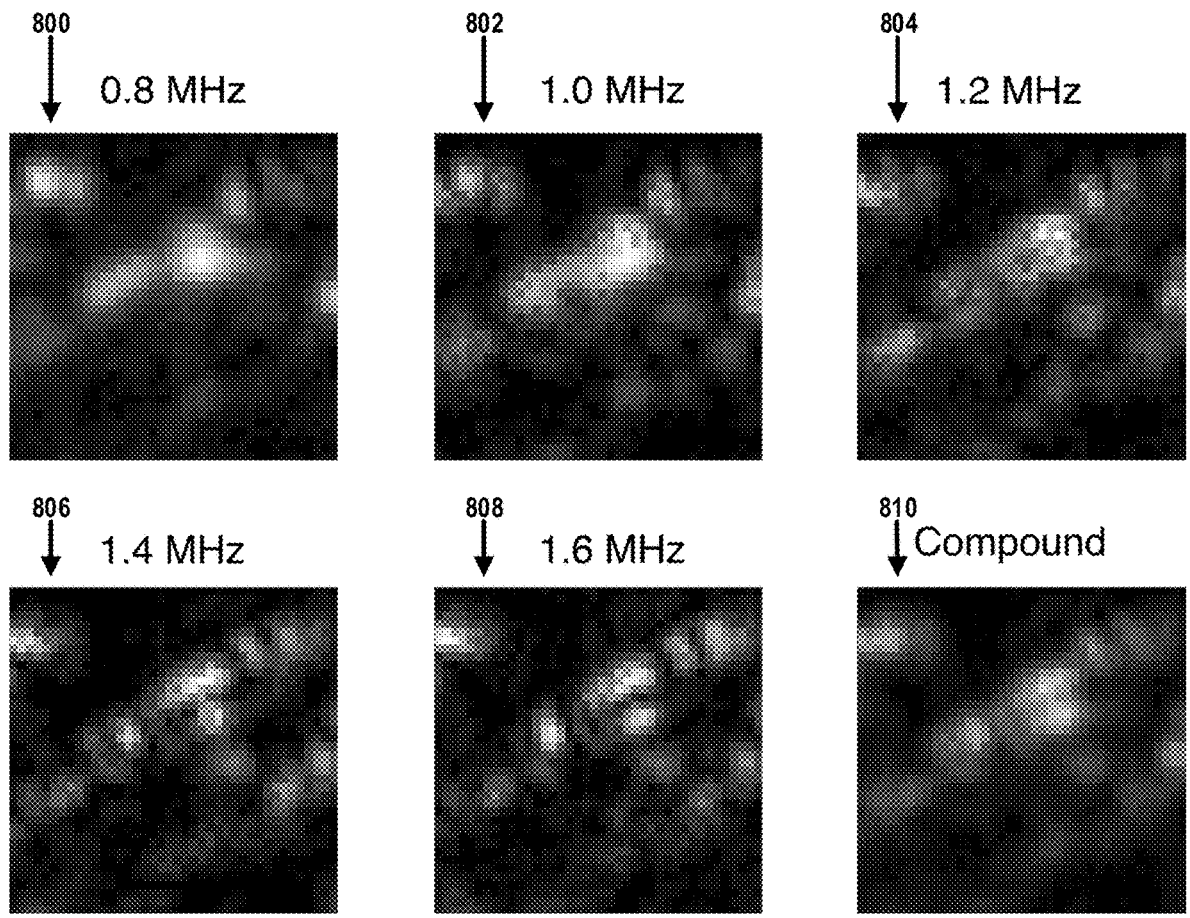
FIG. 8 illustrates nonlinear ultrasonic images obtained at varying difference-frequencies and a compound image obtained from the nonlinear ultrasonic images according to an embodiment of the disclosed technology.

As shown in FIG. 8, the system can obtain difference-frequency images such as images 800, 802, 804, 806, and 808 at multiple difference-frequencies and can then compound the different images into compound image 810 to further suppress residual speckle and noise. The system can tune or vary the difference-frequency for each of the difference-frequency images (e.g., nonlinear ultrasonic images) by varying one or both of the excitation frequencies. Image 802 of FIG. 8 corresponds to the nonlinear image 504 of the 1 cm by 1 cm section of the salmon tissue sample from FIG. 5A. As shown in FIG. 8, compound image 810 exhibits a lower degree of speckle, especially compared to the images 806 and 808 at 1.4 MHz and 1.6 MHz, respectively. The improvement demonstrates the usefulness of frequency compounding to further suppress residual speckle.

Figure 12:
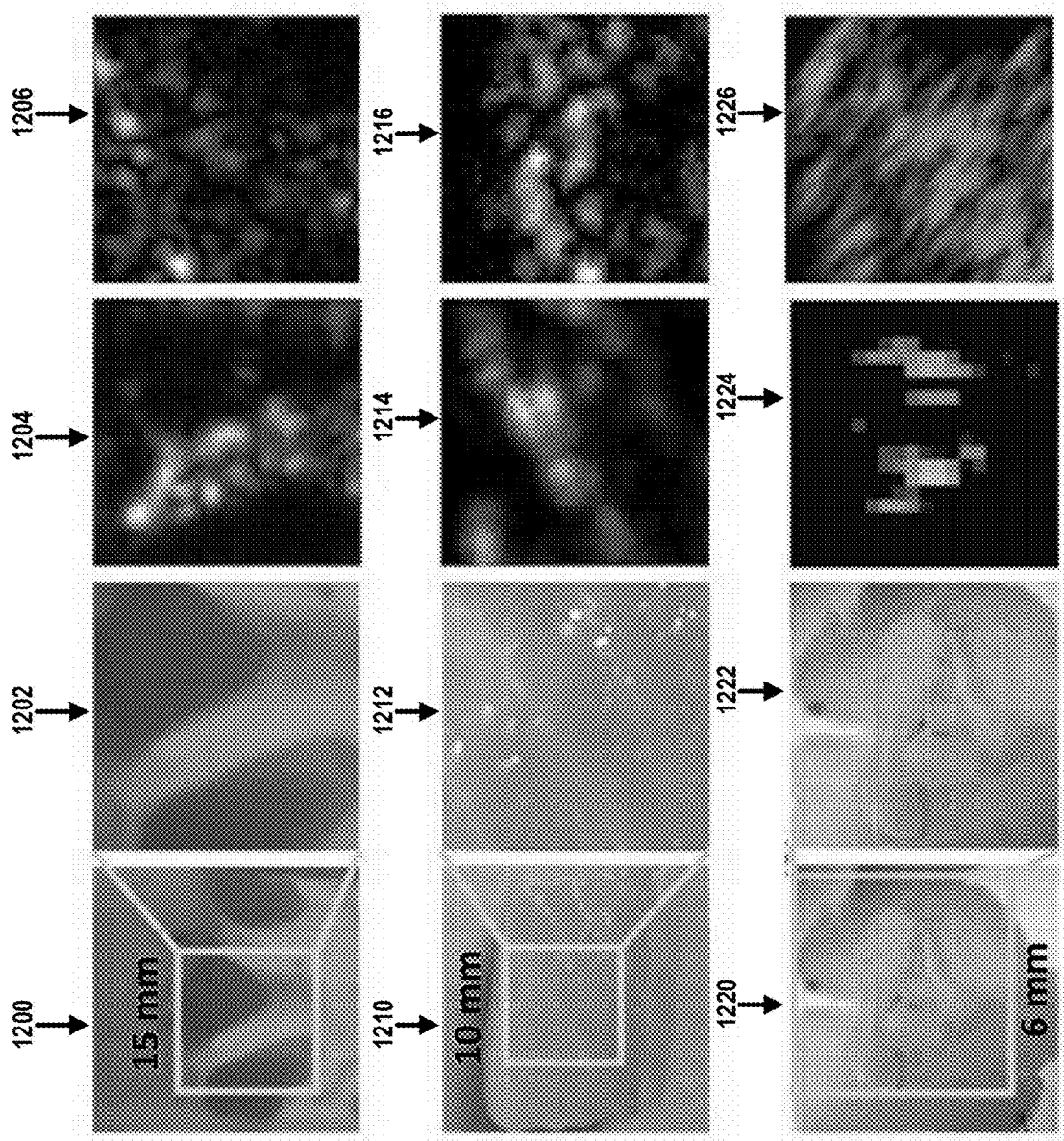
FIG. 12 illustrates optical images of a pig kidney, salmon tissue, and a mouse brain, linear contrast ultrasonic images of the same, and nonlinear contrast ultrasonic images of the same according to an embodiment of the disclosed technology.
Figure 13:
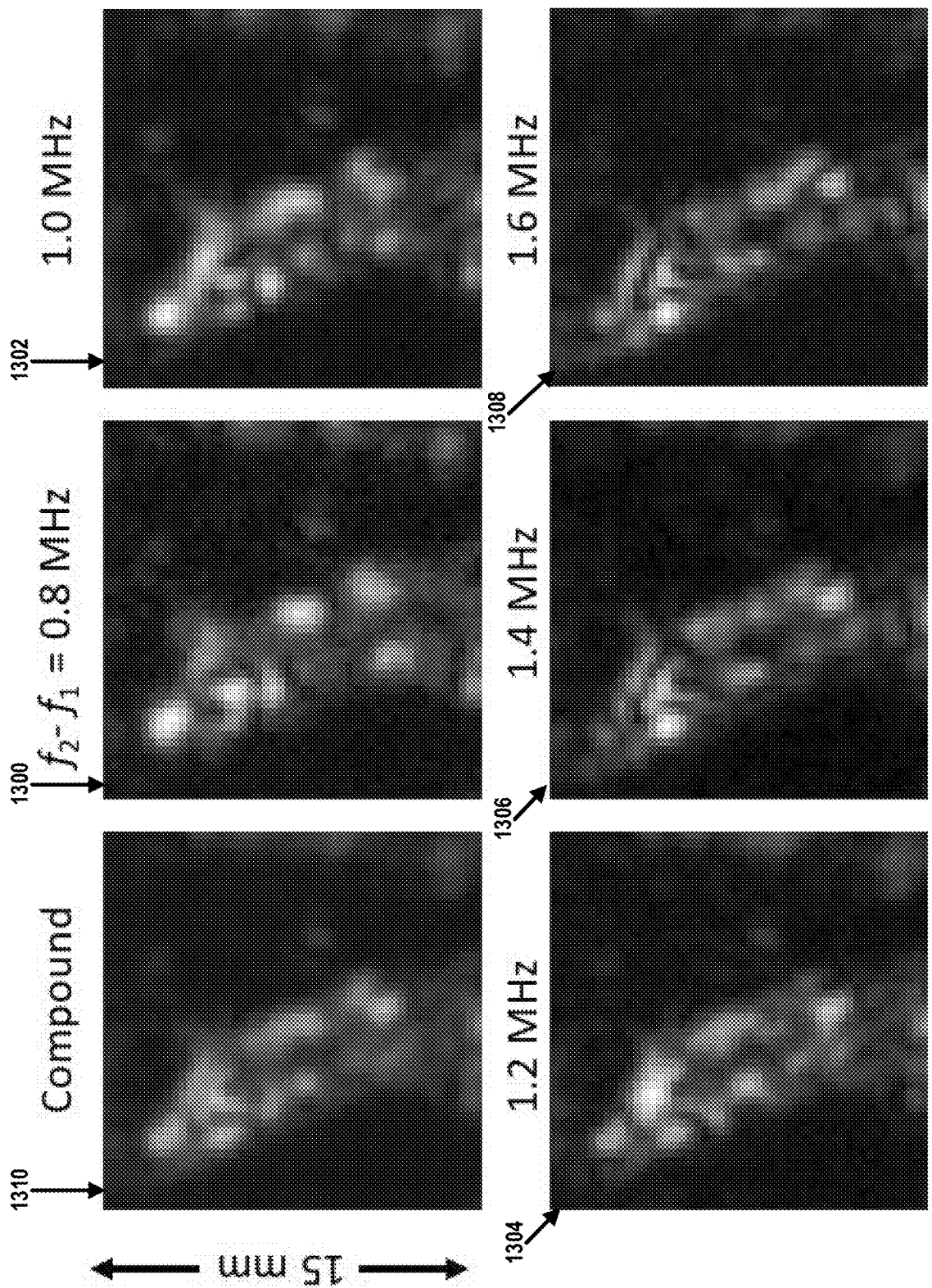
FIG. 13 illustrates nonlinear ultrasonic images of the pig kidney tissue of FIG. 12 obtained at varying difference-frequencies and a compound image obtained from the nonlinear ultrasonic images according to an embodiment of the disclosed technology.

Another example of how the nonlinear ultrasound imaging systems can benefit from frequency or spectral compounding is shown in FIG. 13. As shown in FIG. 13, the system can obtain difference-frequency images such as images 1300, 1302, 1304, 1306, and 1308 at multiple difference-frequencies (e.g., by tuning one or both of the excitation frequencies) and can then compound the different images into compound image 1310 to further suppress residual speckle and noise. As shown in FIG. 13, compound image 1310 exhibits a lower degree of speckle, especially compared to the images 1306 and 1308 at 1.4 MHz and 1.6 MHz, respectively. The image 1302 obtained with a difference frequency of 1.0 MHz corresponds to image 1204 of FIG. 12.

IV. SPATIAL COMPOUNDING IN NONLINEAR ULTRASOUND IMAGING

Spatial compounding of the nonlinear signal can be performed by averaging the images of a region from a number of different angles. An M-fold spatial compounding reduces speckle by up to a factor of $\sqrt{M}$. Frequency and spatial compounding can be combined to achieve a speckle reduction of up to a factor of $\sqrt{MN}$, where N denotes the number of different frequencies compounded together.

In at least some embodiments, spatial or angular compounding can include determining the positions and/or orientations of the nonlinear ultrasound detectors (and even the emitters of the A and A* beams) relative to the subject being imaged for each of the nonlinear images compounded together. The position and/or orientation information may be used by the system in the process of compounding individual ultrasound images (e.g., by registering two or more ultrasound images to each other). When spatially compounding M nonlinear ultrasound images taken by the system from up to M different positions, the system may track the positions of the detectors (and/or emitters) relative to the subject being imaged. Alternatively or in additionally, the system may be able to determine relative positions of a detector (and/or emitter) and the subject being imaged after capturing two or more ultrasound images (e.g., by correlating the images with each other to determine the angular and spatial changes of the detectors between each of the ultrasound images). If desired, the ultrasound system may include inertial sensors, or any other desired position sensors, that provide positional and angular tracking data such that ultrasound images can be compounded together.

V. EXAMPLE EMBODIMENTS OF AN INTEGRATED TRANSDUCER HEAD FOR NONLINEAR ULTRASOUND IMAGING

FIG. 3A illustrates an embodiment of an integrated transducer head 300 that can generate the excitation beams, such as the A and A* beams of FIGS. 1A, 1B, 1C, and/or 2 and that can also receive a nonlinear ultrasound return signal. The transducer head 300 can include two or more linear phased arrays, such as arrays 302 and 304, which may be used for transmitting the A- and A* excitation beams. The array 302 is a first transducer arranged to transmit an ultrasound signal, such as an A-beam of FIG. 1A. The array 304 is a second transducer arranged to transmit a second ultrasound signal, such as the A*-beam, having a different frequency than the first ultrasound signal. Each phased array 302 and 304 can include multiple individually addressable piezoelectric transducer elements. In various embodiments, the spacing between phased arrays 302 and 304 may be varied in order to vary the intersection angle of the excitation beams. In general, wider spacing of the phased arrays 302 and 304 can enable the excitation beams to intersect over a smaller volume, decreasing the size of the voxel and increasing resolution of the system. If desired, a non-integrated transducer head may be provided to facilitate wide separation of the arrays generating the excitation beams. In at least some embodiments, the axial and lateral resolution of the system may be optimized when the excitation beams intersect at approximately a 90 degree angle.

As shown in FIG. 3A, the integrated transducer head 300 can include transducer elements 306, which are configured to detect the difference-frequency signals (e.g., the nonlinear ultrasound return signals). FIG. 3A illustrates transducer elements 306 as round. However, in general, transducer elements such as the elements forming 302, 304, and 306 may be any desired shape. In some embodiments, the element size for detecting the difference-frequency signal, such as the size of elements 306, may be larger than the element size for transmitting the excitation beams, such as the size of elements 302 and 304, which may allow for efficient detection of the longer wavelength at the difference-frequencies. The distribution of the detected signal over the circular elements can be used to further acquire the angular distribution of the nonlinear radiation from each voxel, which in turn gives information about the anisotropy of linear and nonlinear elasticity. The receive aperture may be divided into several sub-apertures, and the signals of the sub-apertures may be obtained separately and averaged to reduce speckle. In an alternative embodiment, the hexagonal receive array 306 of FIG. 3A may be replaced by a linear detector array that is placed in between the two transmission arrays 302 and 304.

The difference frequency sound is detected by a third transducer, such as elements 306 of transducer head 300, which is sensitive to the difference frequencies. Analog filters can be used to attenuate background away from the difference frequency bands. After amplification of the nonlinear signal, the voltage signal can be digitized. To determine the signal from a voxel at depth z along the line scan, the digitized signal can be analyzed in a time window centered at the corresponding time delay, which can be expressed as $t=(z+z')/c$, where $z'$ is the distance from the imaging voxel to the detector and c is the speed of sound. The time window has a duration given approximately by the voxel depth divided by the speed of sound.

Further filtering in the frequency domain can be performed by digital Fourier transformation of the time domain signal and then selecting the frequency band in the frequency domain as discussed above. The nonlinear signal can be obtained by integrating the resulting difference frequency intensity. The speed of data acquisition is not compromised compared to conventional scan since the A-scan time is still determined by the traveling time of the acoustic pulse through the depth of the scan range. Note that the A* transducer may be emitting a continuous stream of ultrasound pulses during the transit time of the A-scan.

Figure 3B:
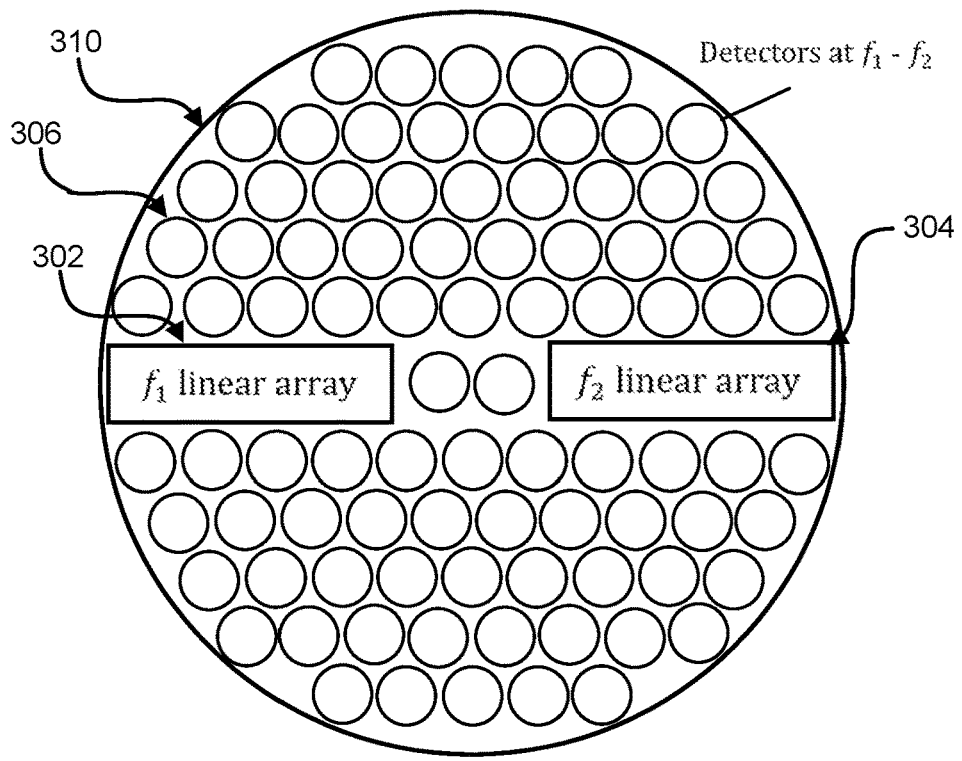
FIG. 3B illustrates another ultrasonic transducer head that includes two linear arrays that can transmit the intersecting beams of FIG. 1A and an array of transducer elements that can receive ultrasonic return signals according to an embodiment of the disclosed technology.

FIG. 3B illustrates another embodiment of an integrated transducer head 310, in which the two linear phased arrays 302 and 304 are separated. The integrated transducer head 310 is similar to the integrated transducer head 300 of FIG. 3A, except that the angle between the intersecting beam is increased, which can improve axial resolution when imaging at greater depths. Transducer elements 306 are also included between the linear phased arrays 302 and 304 in the integrated transducer head 310.

In other embodiments, the excitation beams A and A* may be generated by a single integrated array of ultrasound transducers, which may or may not be a phased array. In other words, the linear phased arrays 302 and 304 may be integrated together. In such embodiments, the integrated array may be able to generate the excitation beams A and A* not only with different angles but from different regions of the integrated array, such that the beams intersect each other at some point within the volume being imaged by the system. If desired, one or both of the linear phased arrays 302 and 304 of an integrated array may be provided in a non-linear shape, such as a planar or circular array, which enables the origin points of the beams to be rotated (alternative, transducer heads such as head 300 and 310 can be rotated in place to achieve a similar effect). In at least some embodiments, the system may receive nonlinear ultrasound signals using receive transducers that are also used in generating one or both of the excitation beams.

VI. PROTOTYPE NONLINEAR ULTRASOUND IMAGING SYSTEM AND RESULTS

Figure 4:
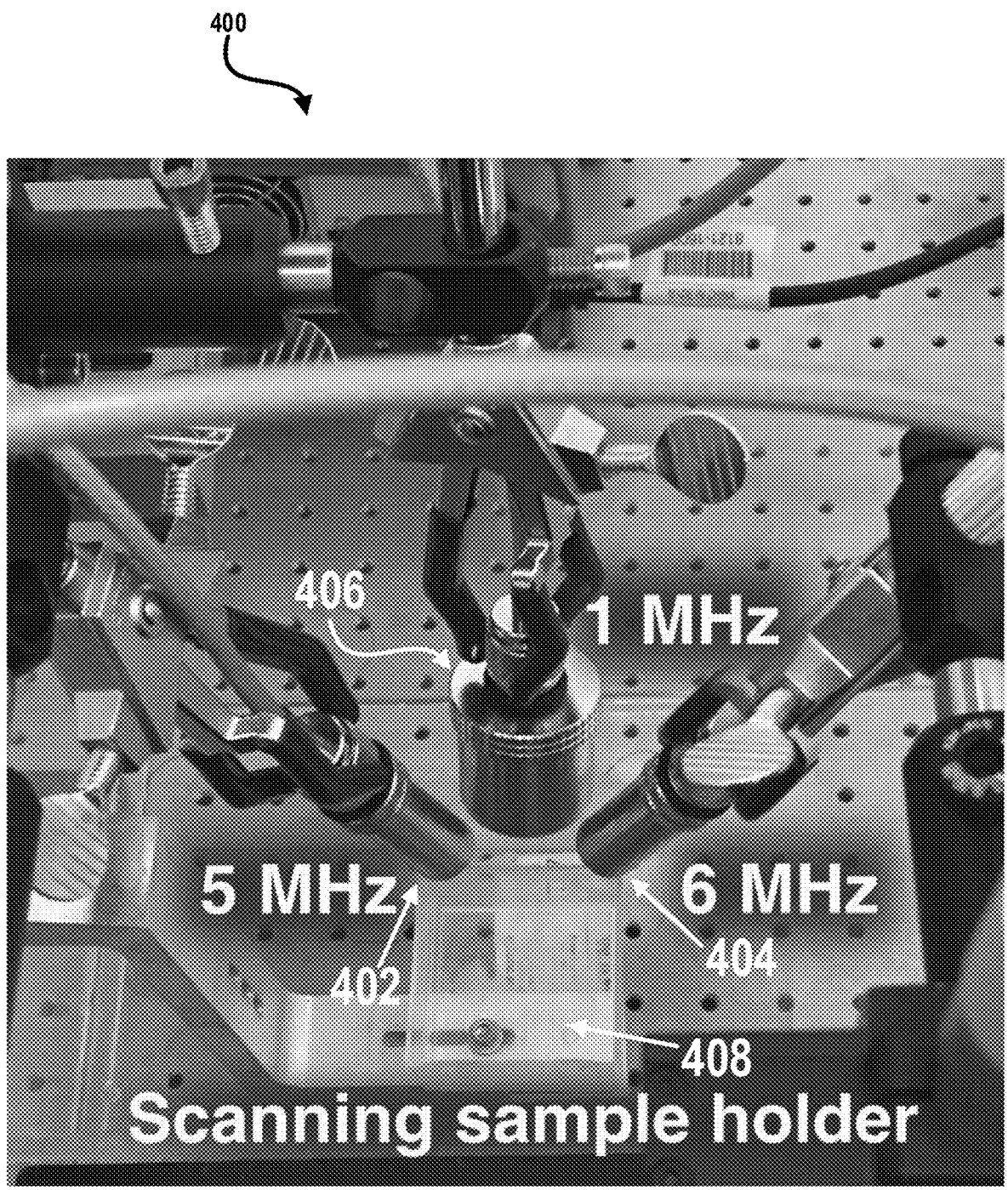
FIG. 4 illustrates a system including multiple ultrasonic transducers for transmitting the intersecting beams of FIG. 1A and receiving ultrasonic return signals according to an embodiment of the disclosed technology.

FIG. 4 illustrates a prototype system 400 for nonlinear ultrasonic imaging using disclosed methods, such as the techniques described in connection with FIGS. 1A-3B. As shown in FIG. 4, ultrasound radiation at 5 MHz and 6 MHz (e.g., $f_1$ and $f_2$) is produced by two piezoelectric transducers 402 and 404, respectively. The center frequencies of the pulses can be controlled by the electrical pulses produced by two arbitrary waveform generators. The electrical pulses at the designated center frequencies can be amplified and can drive the transducers. The acoustic pulses emitted by the two transducers 402 and 404 intersect in both space and time. The intersection of the two excitation beams from transducers 402 and 404 defines an imaging voxel. A difference-frequency signal at $f_{NL}=f_1-f_2=1$ MHz is created in this voxel by the mixing of the two beams from transducers 402 and 404. The difference-frequency signal can be detected with the third piezoelectric transducer 406.

After electrical filtering to remove the echo at the excitation frequency, the difference-frequency echo can be captured by an oscilloscope. Intensity of the difference-frequency signal is extracted in the time window that corresponds to the depth of the intersection of the two excitation beams. By scanning the position of the sample using a motorized stage 408, the excitation voxel is scanned within the sample.

In other arrangements, the positions and/or directions of the excitation beams are scanned in order to scan the excitation voxel within the sample. The positions and/or directions of the excitation beams may be scanned by scanning one or both of the transducers 402 and 404, by beam steering, or by combinations of these and other methods, as examples. If desired, the return signal transducer 406 can be scanned, by moving the transducer 406 and/or through beam steering, to focus the return signal transducer 406 on the excitation voxels as the sample is scanned. By analyzing the detected signal as a function of the sample position, an image can be formed.

Figure 5A:
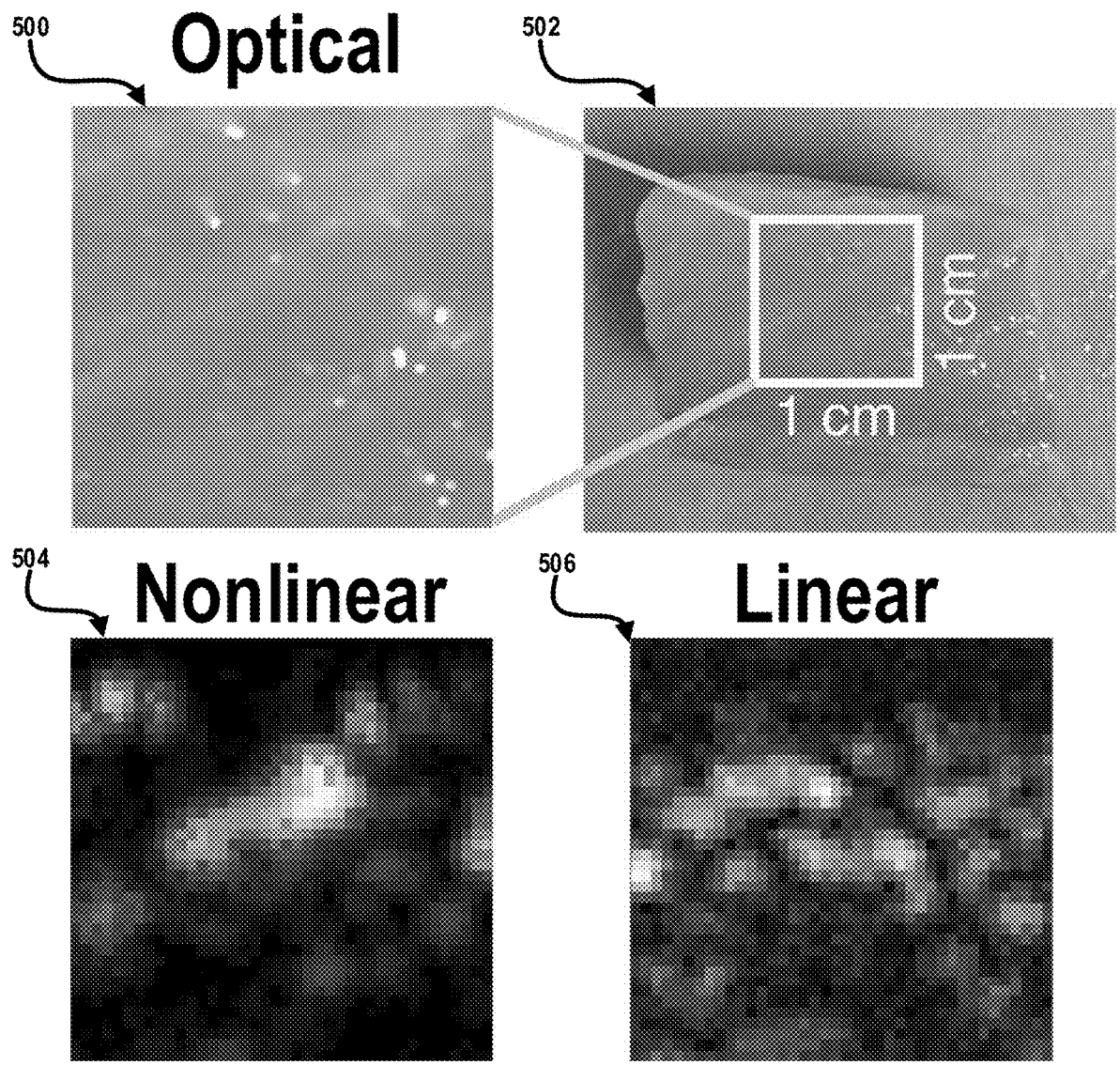
FIG. 5A illustrates optical images of a piece of salmon tissue, a linear ultrasonic image of the salmon tissue, and a nonlinear ultrasonic image of the salmon tissue according to an embodiment of the disclosed technology.

FIG. 5A illustrates the performance of the prototype system 400 of FIG. 4 using salmon tissue as a sample target. FIG. 5A includes an optical image 500 of the salmon tissue used as a sample target, an optical image 502 zoomed in on a 1 cm by 1 cm portion of the sample, a nonlinear image 504 of the 1 cm by 1 cm portion obtained using the techniques described herein (e.g., using the prototype system 400 of FIG. 4 and the techniques described with reference to FIGS. 1A and 1B), and a linear image 506 of the 1 cm by 1 cm portion obtained using conventional B mode ultrasonic imaging techniques. As shown in FIG. 5A, the nonlinear acoustic imaging method is both effective in suppressing speckle and in improving the image contrast of the fat layers in the salmon tissue (see, e.g., the improvement in nonlinear image 504 relative to linear image 506).

Figure 5B:
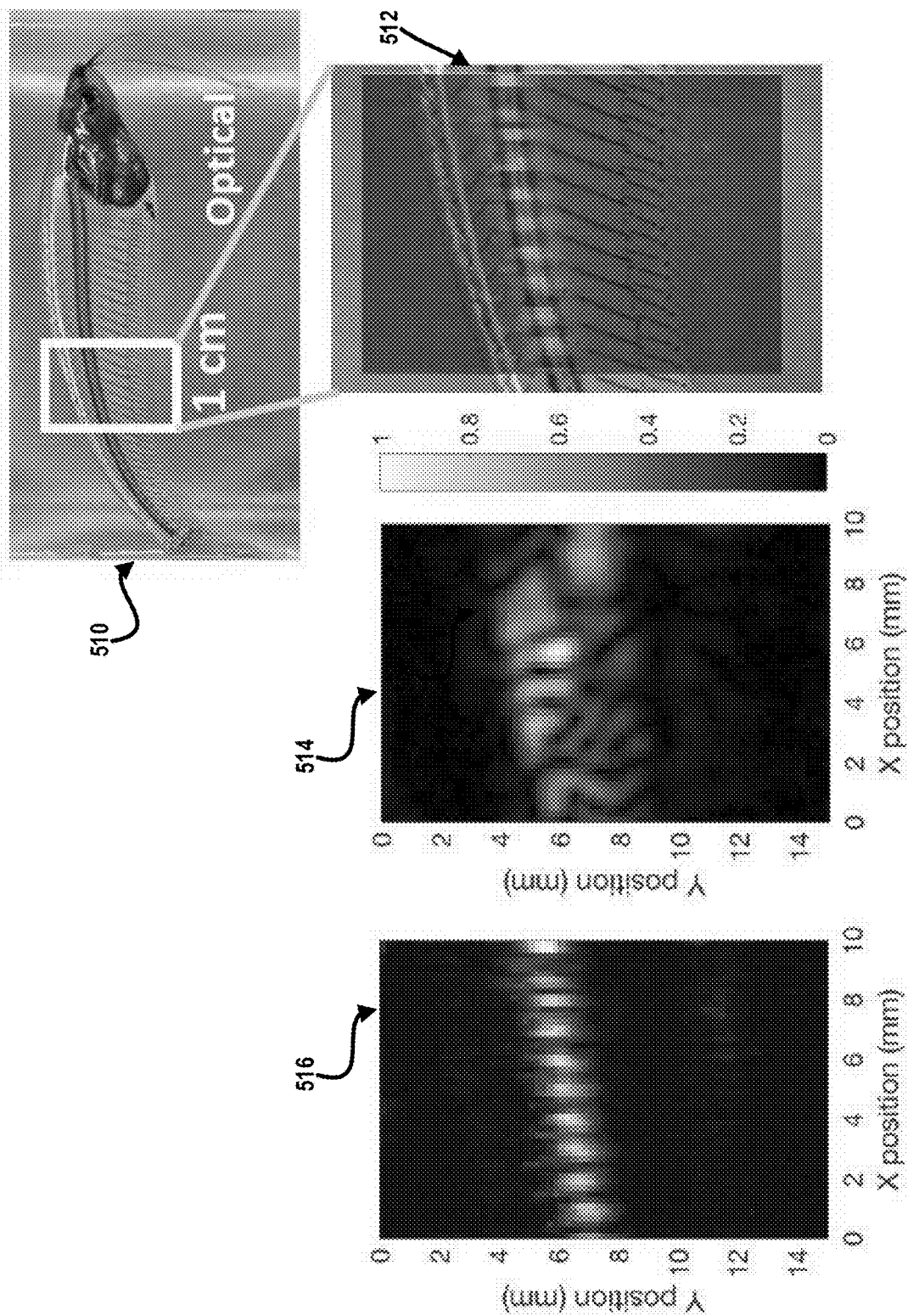
FIG. 5B illustrates optical, linear ultrasound, and nonlinear ultrasound images of a fish with bones.

FIG. 5B illustrates the performance of the prototype system 400 of FIG. 4 using a fish as a sample target. FIG. 5B includes an optical image 510 of the fish used as a sample target, an optical image 512 zoomed in on a 1 cm×1 cm portion of the sample, a linear image 514 of the 1 cm×1 cm portion, and a nonlinear image 516 of the 1 cm×1 cm portion obtained using the techniques described herein (e.g., using the prototype system 400 of FIG. 4 and the techniques of FIGS. 1A and 1B). As shown in FIG. 5A, the nonlinear acoustic imaging method is both effective in suppressing speckle and in improving the image contrast of the bones of the fish (see, e.g., the improvement in nonlinear image 516 relative to linear image 514).

In addition to dramatically improving the image clarity by reducing the speckle noise, the resolution remains defined by the shorter wavelength of the excitation frequencies. The new method can also improve the diffraction limit.

Figure 6:
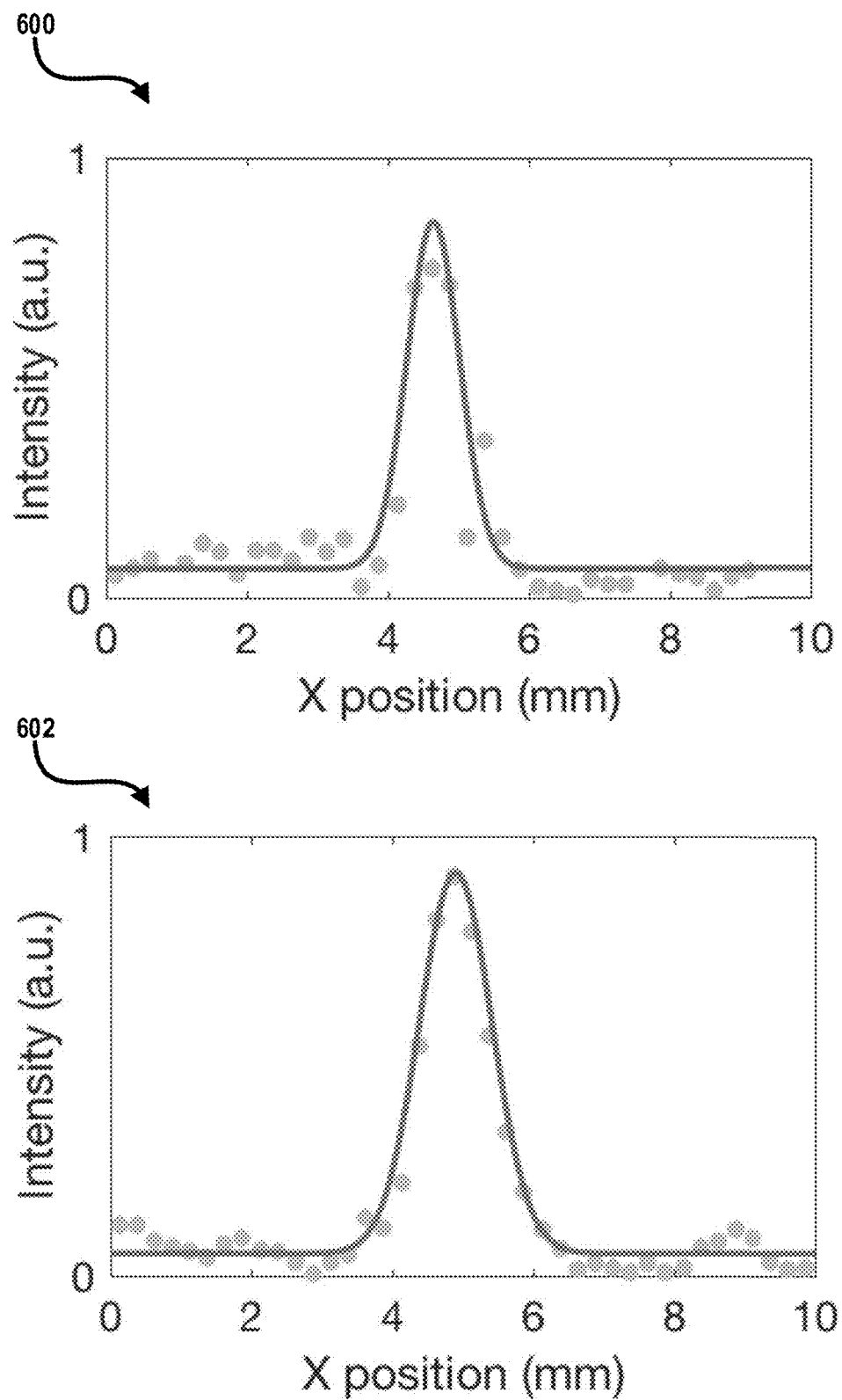
FIG. 6 illustrates graphs of a first line scan obtained using a nonlinear ultrasonic scan and a second line scan obtained using a linear ultrasonic scan according to an embodiment of the disclosed technology.

FIG. 6 illustrates two line scans 600 and 602 obtained using a nonlinear method in accordance with an embodiment and a conventional linear method, respectively. The line scans 600 and 602 are of a fish bone tip with a lateral dimension of ~0.2 mm, which may be significantly smaller than the imaging resolution. As a result, the widths of the line scans 600 and 602 correspond to the diffraction limited resolution of the two methods. The full-width at half maximum of the nonlinear method shown in scan 600 is measured to be 0.89 mm and the full-width at half maximum of the linear method shown in scan 600 is measured to be 1.22 mm. A resolution enhancement of a factor of 1.4 times is demonstrated from the ratio of the two values.

Figure 7:
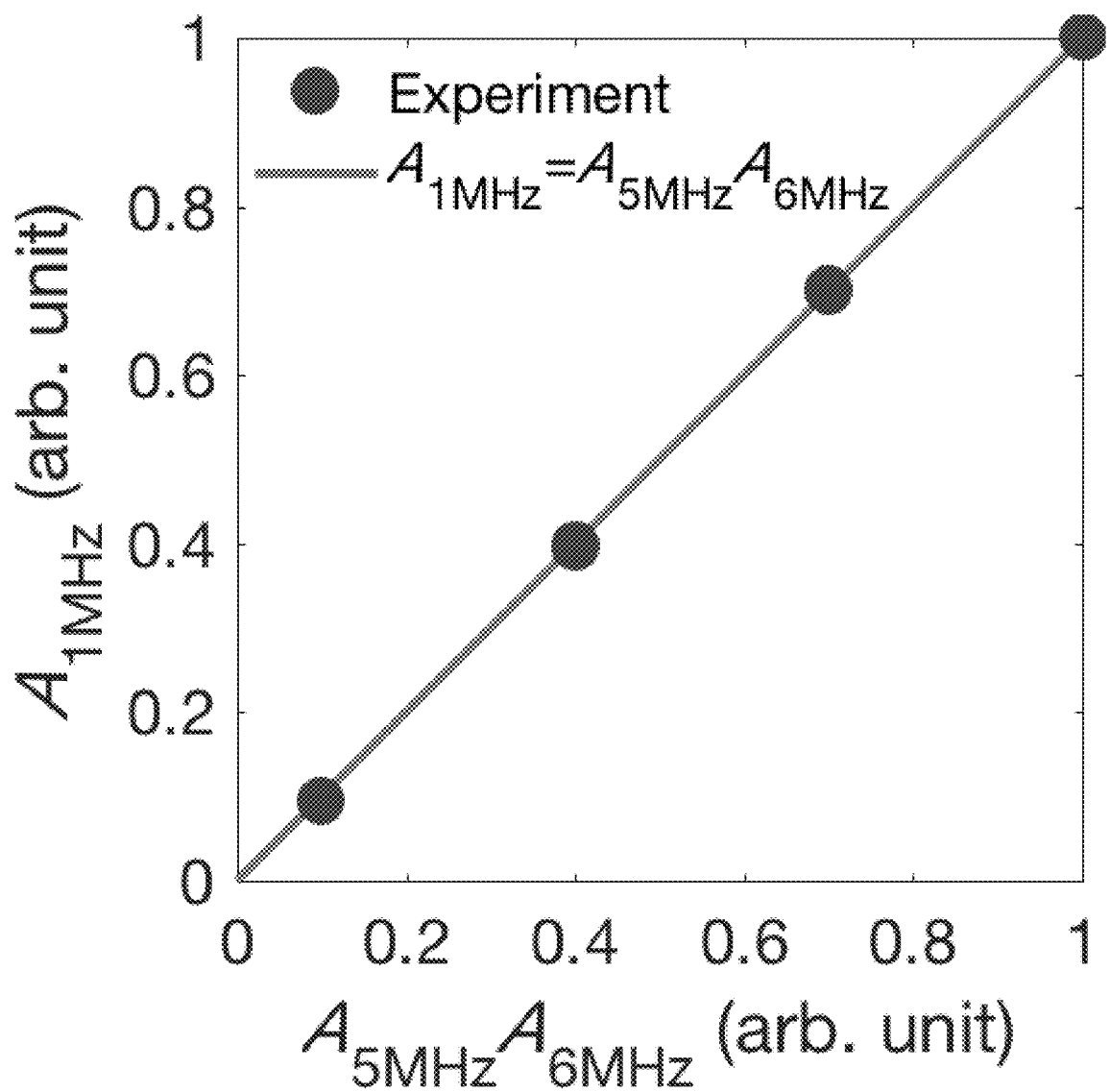
FIG. 7 illustrates a graph of the amplitude of a difference frequency signal as a function of the product of the amplitudes of two intersecting ultrasonic beams according to an embodiment of the disclosed technology.

The resolution enhancement results in part from the amplitude of the difference-frequency signal being proportional to the product of the linear amplitudes of the two excitation pulses. In particular, this relationship is shown in the graph of FIG. 7, which illustrates the amplitude of the difference frequency signal as a function of the product of the amplitudes of the two intersecting excitation beams. Because of this relationship, the amplitude of the difference-frequency signal decays faster away from the focal point as compared to the individual excitations (e.g., as compared to ultrasound utilizing a single excitation beam). In other words, the difference frequency signal is highly concentrated at the region of intersection of the individual excitation beams and falls off sharply away from the region of intersection. This effect increases the effective resolution of the system. The same mechanism also accounts for the improved resolution in harmonic imaging modes.

In addition to the improvement factors discussed above, the nonlinear ultrasound imaging system can utilize shorter wavelength (i.e., higher frequency) excitation beams than comparable linear ultrasound imaging systems. As a result, the nonlinear ultrasound imaging systems disclosed herein may have improved resolution. In particular, the attenuation rate (e.g., dB per centimeter of depth) of typical ultrasound targets, such as various body parts in medical ultrasounds, generally increases with higher frequencies. Thus, a typical linear ultrasound imaging system imaging a patient's liver needs to image to an approximately 20 cm depth. At a typical ultrasound frequency of 2.5 MHz, a patient's abdomen absorbs ultrasound at a rate of 2.2 dB per centimeter for a total one-way reduction of 44 dB reduction (e.g., an efficiency of 0.63%) at 20 centimeters of depth. Since the return signal in linear ultrasound systems is at the excitation frequency, the return signal also experiences a one-way reduction of 44 dB. As a result, the total loss is about 88 dB (e.g., an efficiency of $4\times10^{-5}$)

With the nonlinear ultrasound systems disclosed herein, the return signal may be at a significantly lower frequency. If, as an example, the return signal is at 0.8 MHz, the absorption rate for the abdomen drops to 0.6 dB per cm or 12 dB total (e.g., an efficiency in transmission of 0.25%). Assuming that the total loss remains at 88 dB, the significantly lower absorption rate for the return signal means that the system can tolerate a significantly higher absorption rate for the excitation signals. Continuing the previous example, the system could tolerate a 76 dB loss in the excitation signals (e.g., 88 dB total loss less the 12 dB return loss). Because of this higher tolerance, the system can utilize even higher excitation frequencies (than the linear systems at 2.5 MHz), such as 4 MHz. In general, resolution and penetration depth scale with the input frequencies. Thus, the nonlinear systems, utilizing higher excitation frequencies enabled by the lower absorption rate of the relatively low frequency return signal, may have a resolution improvement of about a factor of 1.6 over linear systems. In at least some embodiments, the nonlinear systems may have an expected resolution of about 440 micrometers when the lower frequency excitation beam is at 4 MHz.

VII. SIMULATED ACOUSTIC FIELDS FOR A NONLINEAR ULTRASOUND SYSTEM

Figure 9:
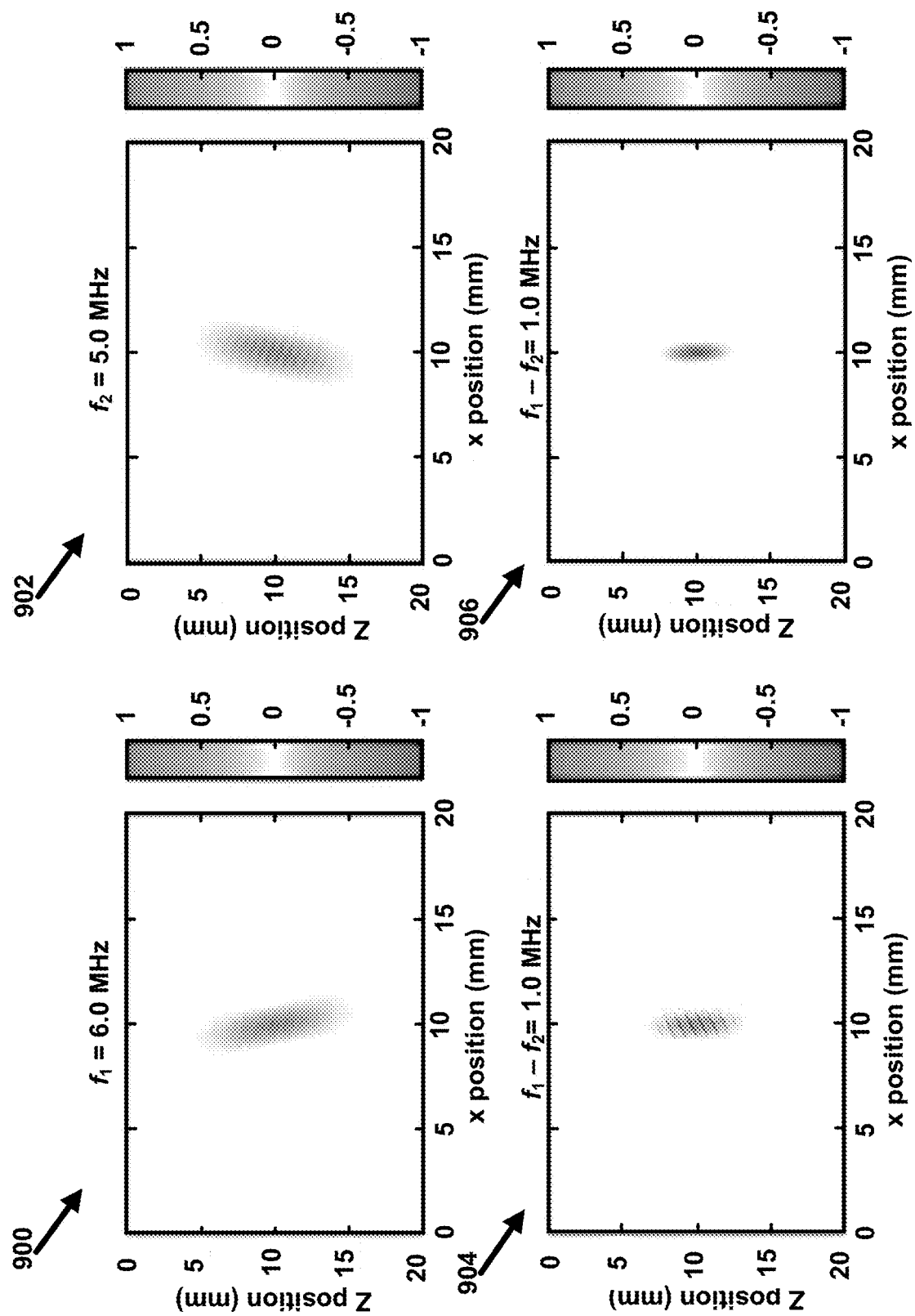
FIG. 9 illustrates graphs of simulated acoustic fields for a first of the intersecting beams of FIG. 1A, a second of the intersecting beams of FIG. 1A, nonlinear emission from an intersection voxel, and the spatial distribution of the intensity of the nonlinear emission according to an embodiment of the disclosed technology.

FIG. 9 shows the computer simulated acoustic fields for the two excitation pulses (plots 900 and 902), and the nonlinear emission from the intersection voxel (plot 904). The simulation uses $f_1$=6.0 MHz and $f_2$=5.0 MHz for the two excitation pulses and the angle between their directions of propagation is 15°. $\Delta f$=0.1 MHz is used. The transverse dimension of the nonlinear voxel is smaller than the excitation pulses by a factor of about 1.4. The longitudinal dimension of the nonlinear voxel is larger than the transverse dimension by about 4 times. Increasing the angle between the two pulses can improve the longitudinal resolution. Plot 906 shows the spatial distribution of the intensity of the nonlinear emission.

VIII. A NONLINEAR ULTRASOUND SYSTEM

Figure 10:
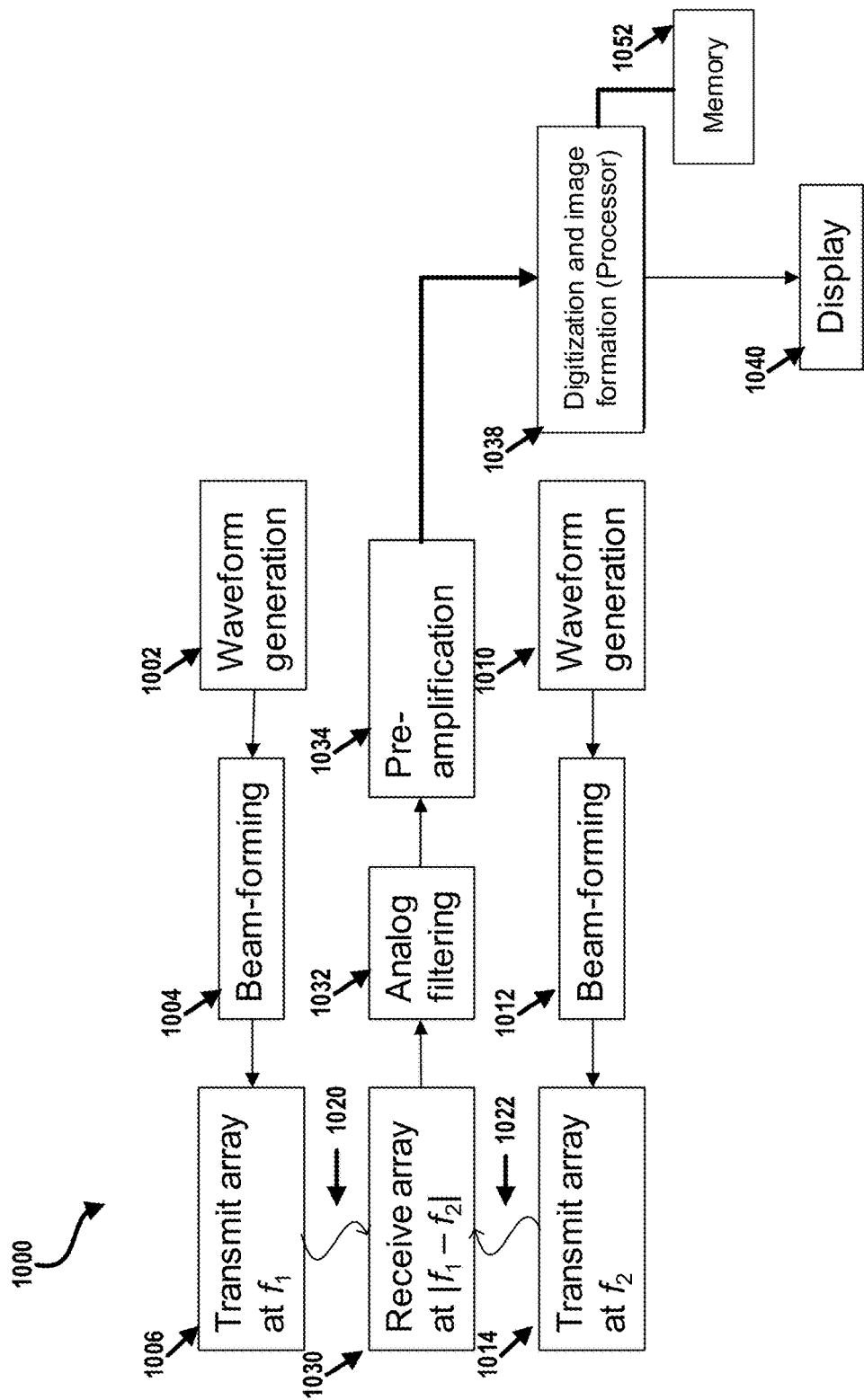
FIG. 10 is a block diagram of a system for nonlinear ultrasonic imaging according to an embodiment of the disclosed technology.

FIG. 10 is a schematic block diagram of ultrasound imaging system 1000. The ultrasound imaging system 1000 can generate ultrasound images with nonlinear contrast and reduced speckle. The system 1000 includes transducers including transmit arrays 1006 and 1014 and receive array 1030. The system also includes a processing circuit, such as processor 1038, arranged to generate an ultrasound image based on echoes received at the receive array 1030.

The processing circuit, which may be a processor, can generate ultrasound images in accordance with any suitable principles and advantages discussed herein. The processing circuit can perform a variety of signal processing functions such as frequency compounding, spatial compounding, voxel differentiation, filtering, or any other suitable processing functions for generating an ultrasound signal from received echoes. The processing circuit can include any suitable circuitry arranged to perform such signal processing. As illustrated, the processing circuit may include an analog filtering circuit 1032, a pre-amplification component 1034, and a digitization and image formation component 1038. The processing circuitry may also include waveform generation components 1002 and 1010 and beam-forming components 1004 and 1012.

The system 1000 can include one or more waveform generation components, such as wave form generation components 1002 and 1010. The waveform generation components 1002 and 1010 can generate the excitation signals used in exciting nonlinear emissions from voxels of an object being imaged by the system 1000. The excitation signals used to generate the A and A* beams are shown in FIG. 1A as an example. The waveform generators 1002 and/or 1010 can be used to generate a frequency modulated ultrasound signal (e.g., to facilitate distinguishing adjacent voxels, to facilitate frequency compounding, etc.). As one example, waveform generation component 1002 may generate excitation waveforms for the A beam of FIG. 1A, while waveform generation component 1010 may generate excitation waveforms for the A* beam of FIG. 1A.

Beam-forming components 1004 and 1012 can apply beam-forming to the waveforms generated by components 1002 and 1010, respectively. As an example, beam-forming components 1004 and 1012 can cause the resulting A and A* beams to be properly steered such that the beams intersect and excite the desired voxels as a function of time.

Beam-forming is a technique used with antenna arrays for transmitting or receiving signals with a controllable directionality. The direction of signals transmitted by an array (or the sensitivity of the array to signals from a particular direction) is altered by adjusting signal delays for the various antenna elements that form the array, such that signals transmitted at or received from desired angles experience constructive interference and signals outside those desired angles experience destructive interference. Beam-forming may be accomplished via hardware or software (e.g., by adjusting hardware delay elements or by delaying signals for particular antenna elements via software).

Transmit arrays 1006 and 1014 can receive the beam-formed waveforms and transmit the excitation pulses into a medium being imaged by the system 1000, as shown schematically by pulses 1020 and 1022. Transmit array 1006 may transmit pulses at frequencies $f_1$ corresponding to the A beam of FIG. 1A, while transmit array 1014 may transmit pulses at frequencies $f_2$ corresponding to the A* beam of FIG. 1A.

Receive array 1030 can receive the nonlinear difference signal from the excited voxels. In particular, receive array 1030 may receive return signals at the difference frequency of the difference between $f_1$ and $f_2$.

Analog filtering circuit 1032 can filter the incoming signals from the receive array 1030. As examples, the analog filtering circuit 1032 may include low-pass, high-pass, and/or band-pass filters configured to reject or block linear echoes at the excitation frequencies $f_2$ and $f_2$, to reject or block harmonics of the excitation frequencies, to pass or accept signals at the difference frequency and to apply any other desired filtering.

Pre-amplification component 1034 may amplify the incoming signals from the analog filtering circuit 1032.

Digitization and image formation component 1038 may digitize the incoming signals from the receive array 1030 and can integrate or combine signals received over time into an ultrasound image. The digitization and image formation component 1038 may include a receive beam-forming component that uses beam-forming techniques to focus on a particular voxel or region of the object being imaged by the system 1000. In at least some embodiments, receive beam-forming can be performed digitally (e.g., after digitization of the incoming signals, but before image formation). In at least some other embodiments, receive beam-forming may be performed on incoming analog signals prior to digitization. The ultrasound image created by component 1038 may be a B-mode ultrasound image generated from the nonlinear signals of individual voxels. In at least some embodiments, component 1038 may be a processor configured with software to digitize incoming signals and combine those signals into an ultrasound image. Component 1038 may be coupled to memory 1052.

Display 1040 can visually present or otherwise provide the ultrasound image formed by component 1038 to a user. The display 1040 can be any suitable display arranged to visually present an ultrasound image, such as any of the ultrasound images shown in the drawings.

The nonlinear ultrasound imaging system 1000 may include memory 1052. Memory 1052 may store constructed images, processing results, transmit and receive control instructions, beamforming parameters, and software instructions, as examples.

IX. EXAMPLE RESULTS FOR NONLINEAR CONTRAST ULTRASOUND SYSTEM

Figure 11:
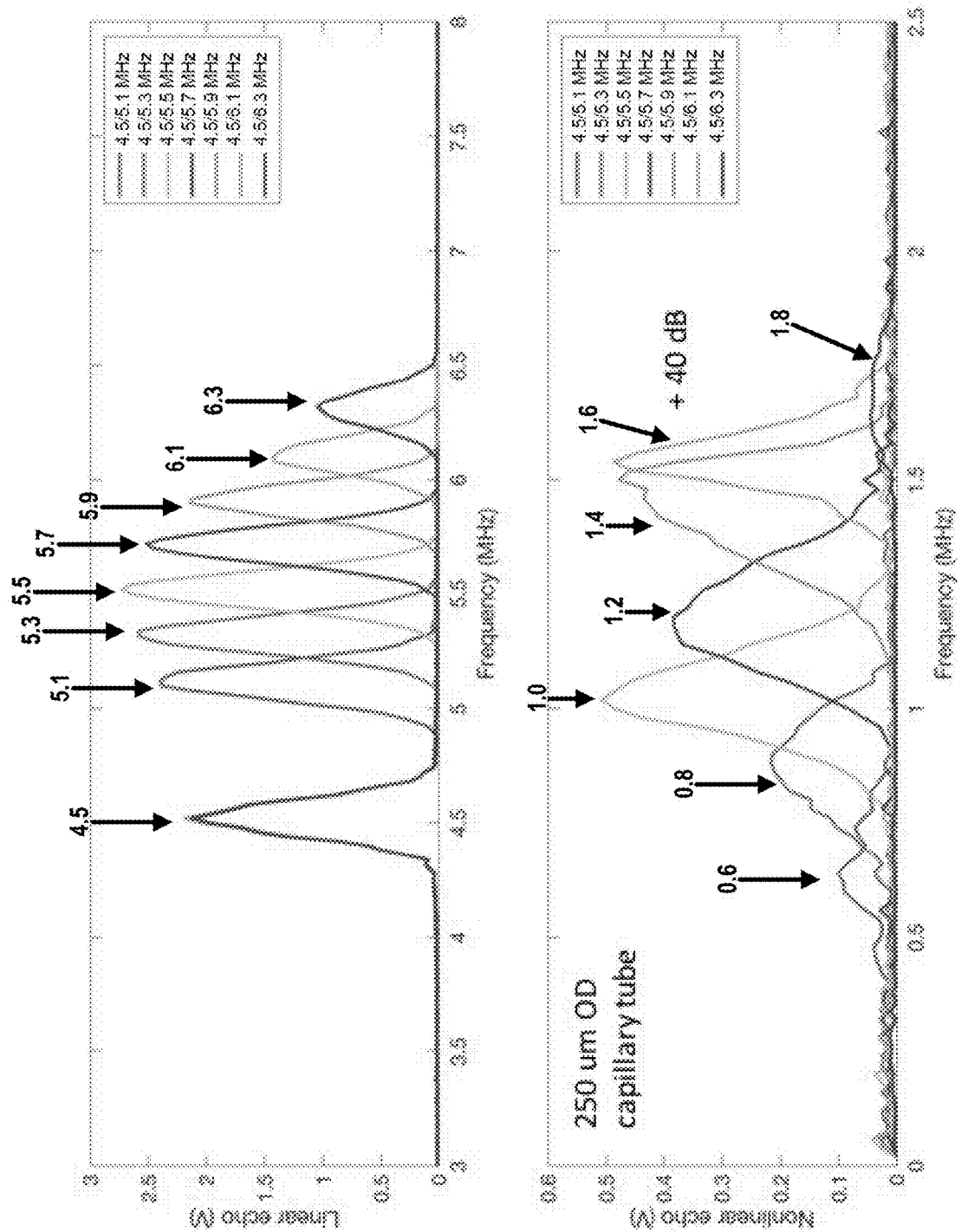
FIG. 11 shows the spectra of the excitation Gaussian pulses (linear echo) and the spectra of the nonlinear signal (nonlinear echo) according to an embodiment of the disclosed technology.

FIG. 11 illustrates the spectrum of the excitation Gaussian pulses and of the nonlinear return signals or echoes obtained using the prototype system 400 of FIG. 4, for combinations of various excitation pulse frequencies, on a capillary tube having a 250 micrometer outer diameter. The center frequency of the nonlinear echo is shown to be centered around the difference of the center frequencies of the excitation pulses. The spectral line shape of the difference frequency echo is affected by the response function of the receiving transducer. The modifications are primarily modulations of the overall amplitudes, as the bandwidth of the nonlinear signal is about 5 times smaller than the bandwidth of the transducer. More subtle modifications of the line shape can be seen due to the variation of the receiving transducer response within the bandwidth of the nonlinear pulse.

FIG. 11 illustrates excitation pulses and and nonlinear return signals with a first excitation beam at 4.5 MHz intersecting with a second excitation beam at 0.2 MHz steps from 5.1 MHz to 6.3 MHz. Thus, FIG. 11 illustrates the excitation pulses at the first excitation frequency of 4.5 MHz (see, e.g., the overlapping peaks at 4.5 MHz) and at each of the variations of the second excitation frequency (e.g., 5.1 MHz to 6.3 MHz in 0.2 MHz steps) and also illustrates the nonlinear return signals at the difference frequencies of 0.6 MHz, 0.8 MHz, 1.0 MHz, 1.2 MHz, 1.4 MHz, 1.6 MHz, and 1.8 MHz. The nonlinear return signals are labeled according to the difference frequencies, namely 0.6, 0.8, 1.0, 1.2, 1.4, 1.6, and 1.8, while the excitation pulses are labeled according to their respective frequencies.

FIG. 12 illustrates example results obtained using a nonlinear contrast ultrasound system. As shown in FIG. 12, the system was used to image a portion of a pig kidney, a portion of salmon tissue, and a mouse brain. FIG. 12 shows that nonlinear contrast images in accordance with the principles and advantages discussed herein can provide clearer ultrasound images than corresponding linear contrast ultrasound images.

Image 1200 is an optical image of the pig kidney sample and an enlarged optical image focused on a 1.5 cm by 1.5 cm section of the pig kidney sample is shown in image 1202. The nonlinear contrast ultrasound system was used to obtain the nonlinear image 1204 of the 1.5 cm by 1.5 cm section of pig kidney. In nonlinear image 1204, the minor calyx is clearly seen. In contrast, the minor calyx is unidentifiable in the linear contrast image 1206.

Image 1210 is an optical image of the salmon tissue sample and an enlarged optical image focused on a 1.0 cm by 1.0 cm section of the salmon tissue is shown in image 1212. The nonlinear contrast ultrasound system was used to obtain the nonlinear image 1214 of the 1.0 cm by 1.0 cm section of salmon tissue. In nonlinear image 1214, the fat layers in the salmon tissue are visible, while these fat layers are not visible over noise in the linear contrast image 1216.

Image 1220 is an optical image of the mouse brain sample, which includes a millimeter sized glioblastoma tumor, and an enlarged optical image focused on a 0.6 cm by 0.6 cm section of the mouse brain is shown in image 1222. The nonlinear contrast ultrasound system was used to obtain the nonlinear image 1224 of the 0.6 cm by 0.6 cm section of mouse brain. In nonlinear image 1224, the millimeter sized glioblastoma tumors are visible, while these tumors are not visible over noise in the linear contrast image 1226.

X. IMAGING FLUID FLOWS IN A NONLINEAR ULTRASOUND IMAGING SYSTEM

Figure 14A:
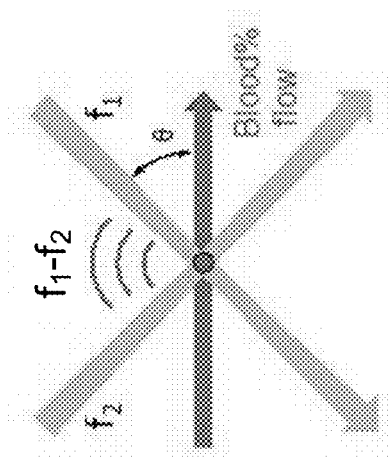
FIG. 14A is a diagram associated with a nonlinear ultrasound imaging system measuring fluid flow according to an embodiment of the disclosed technology.

The nonlinear ultrasound imaging systems and methods disclosed herein can be used in imaging fluid flows, such as blood flow in a patient. When imaging fluid flows, the nonlinear return signal is subjected to a Doppler shift, due to the motion of the fluid, given by $\Delta f_{Doppler}=(f_1-f_2)+(\Delta f_{1D}+\Delta f_{2D})$, where $\Delta f_{1D}/f_1=(v_{blood\ flow}/v_{sound})\cos\theta$, as shown in FIG. 14A. The geometrically defined voxel may also be free from the aliasing artifact in the conventional pulse width and color Doppler.

Figure 14B:
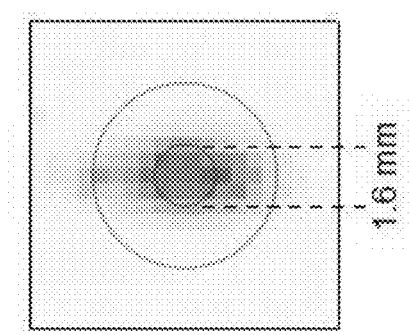
FIG. 14B illustrates a nonlinear ultrasonic image of fluid flow through tubing according to an embodiment of the disclosed technology.

In one example, a micro-bubble contrast agent (in particular, SonoVue from Bracco Inc.) at a diluted concentration allowed by the FDA was used to enhance a nonlinear signal in a blood flow through tubing (having a 1.6 mm inner diameter) and the nonlinear ultrasound imaging system was used to obtain the nonlinear image shown in FIG. 14B depicting the spatial distribution of the nonlinear Doppler signal intensity. As shown in FIG. 14B, the image is consistent with the expected image from the moving bubbles confined within the tubing and the image shows a spatial resolution of 0.75 mm by 1.2 mm.

Figure 14C:
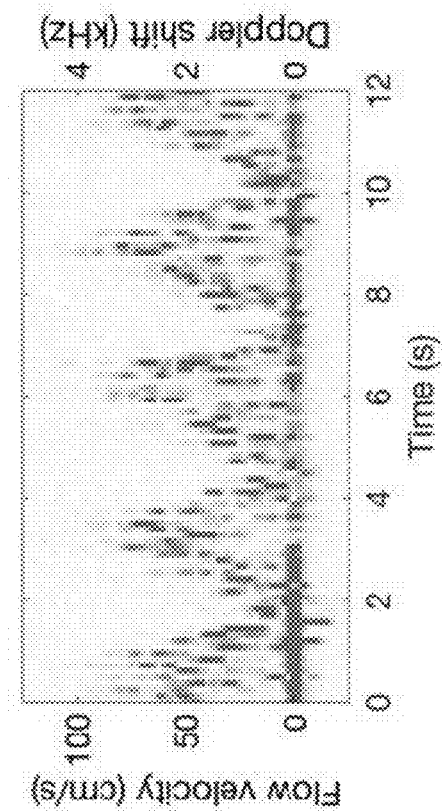
FIG. 14C is a graph of flow velocity over time as measured using a nonlinear ultrasound imaging system according to an embodiment of the disclosed technology.

The Doppler shift (right y-axis) and corresponding flow velocity (left y-axis) as a function of time (x-axis) at the center of the tubing is shown in FIG. 14C. When capturing the image of FIG. 14C, the flow velocity was modulated at a frequency of about ⅓ Hz. When measuring blood flow in a live animal or patient, the signal acquisition can be synchronized with breathing and heartbeat to reduce motion artifacts. The direct measurement of blood flow at the locations of regions of interest, such as partial coronary blockages throughout the heart, may be non-invasively imaged at high levels of quality with the nonlinear ultrasound imaging systems provided herein.

XI. A Method of Nonlinear Imaging

Figure 15:
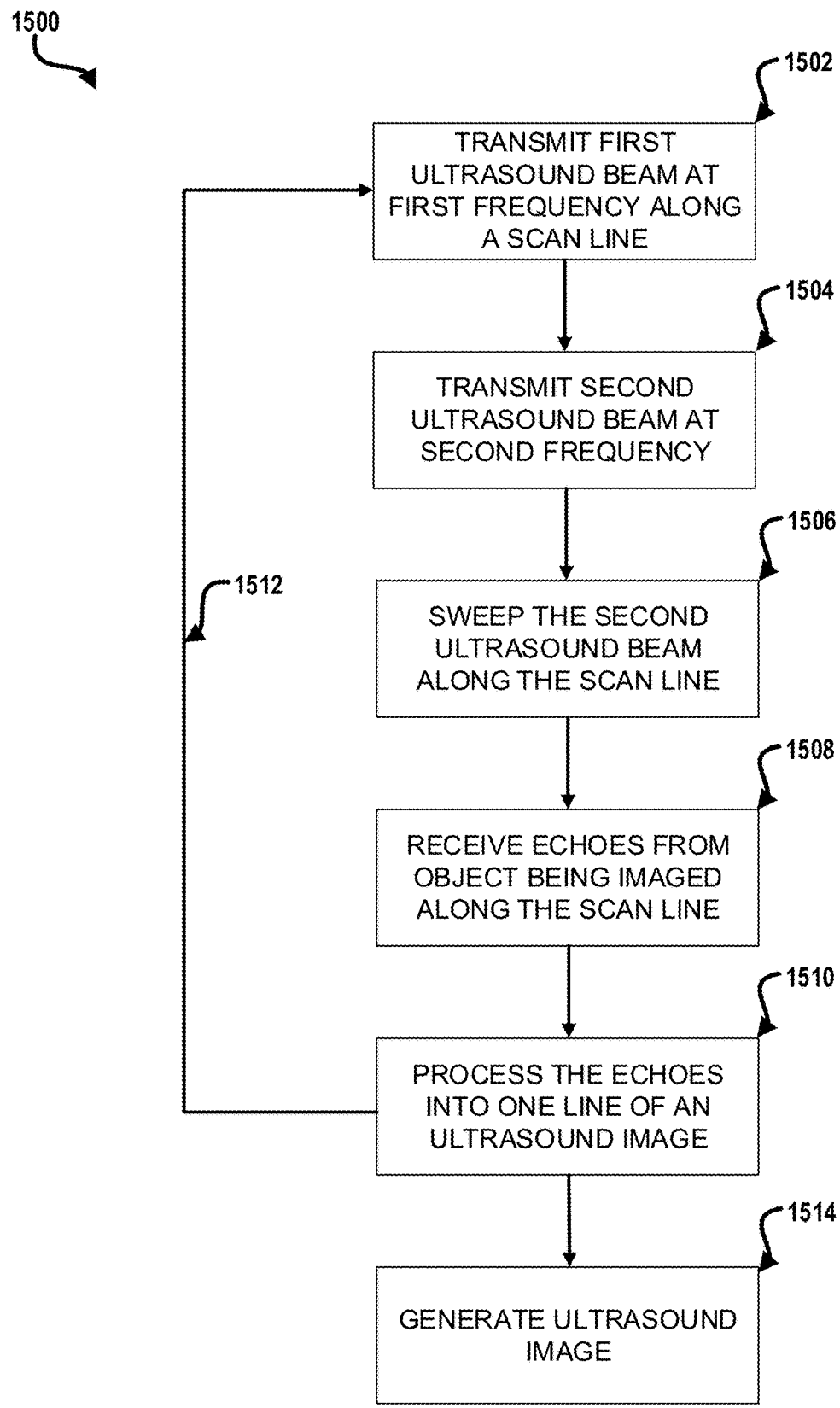
FIG. 15 is a flowchart of a method of nonlinear ultrasound imaging according to an embodiment of the disclosed technology.

FIG. 15 is a flowchart of method 1500 of nonlinear imaging according to an embodiment of the disclosed technology.

In block 1502, method 1500 transmits a first ultrasound beam at a first frequency along a scan line (e.g., transmits one or more ultrasound pulses in the A beam along a given scan line in the B-scan sweep, as depicted in FIG. 1A).

In block 1504, method 1500 transmits a second ultrasound beam at a second frequency. As an example, block 1504 may involve transmitting one or more ultrasound pulses in the A* beam. The pulses transmitted in block 1504 may be timed to intersect with corresponding pulses of the A beam at one or more voxels being imaged, as depicted in FIG. 1A.

In block 1506, method 1500 sweeps the second ultrasound beam along the scan line of the first ultrasound beam.

As an example, block 1506 may involve sweeping the A* beam along the scan line of the A beam (e.g., along the current scan line of the B-scan sweep) as illustrated in FIG. 1A.

In block 1508, method 1500 receives echoes along the scan line from the object being imaged. The echoes may result from nonlinear interactions of the first and second scan beams and may have a frequency equal to the difference of the first and second frequency.

In block 1510, method 1500 processes the echoes into one line of an ultrasound image (e.g., a B-scan image).

As indicated by arrow 1512, blocks 1502-1510 may be repeated for multiple scan lines. In particular, the A beam may be swept along the B-scan sweep direction 110, as illustrated in FIG. 1A, and the A* beam may be adjusted to continue to sweep along the new scan lines of the A beam. In this manner, each of the lines of a B-mode image can be obtained.

In block 1514, method 1500 combines the lines of the ultrasound image, obtains via multiple iterations of blocks 1502-1510, into an ultrasound image, such as a B mode image. The B mode image may be stored in memory or storage and may be displayed or otherwise provided to a user.

In at least some embodiments, the blocks of method 1500 may be performed at least partially in parallel. As an example, blocks 1502, 1504, and 1506 may be performed substantially in parallel such that the transmitted pulses in the first and second ultrasound beams intersect in time and space at the desired voxels being imaged, for example, as depicted in FIG. 1A. Similarly, blocks such as block 1508 and 1510 can be performed substantially in parallel, but delayed with respect to blocks 1502, 1504, and 1506 to account for the round-trip time of the ultrasound beams to and from the voxels being imaged.

XII. CONCLUSION

While certain embodiments have been described, these embodiments have been presented by way of example only, and are not intended to limit the scope of the disclosure. Indeed, the novel devices, systems, apparatus, and methods described herein may be embodied in a variety of other forms. The principles and advantages of the embodiments can be used for any other suitable devices, systems, apparatuses, and/or methods that could benefit from such principles and advantages. Furthermore, various omissions, substitutions and changes in the form of the methods and systems described herein may be made without departing from the spirit of the disclosure. All possible combinations and sub combinations are intended to fall within the scope of this disclosure. For example, while blocks are presented in a given arrangement, alternative embodiments may perform similar functionalities with different components and/or circuit topologies, and some blocks may be deleted, moved, added, subdivided, combined, and/or modified. Each of these blocks may be implemented in a variety of different ways. As another example, methods discussed herein can be performed in any suitable order. Any suitable combination of the elements and acts of the various embodiments described above can be combined to provide further embodiments.

What is claimed is:

1. A method of nonlinear ultrasound imaging, the method comprising:
    transmitting a first ultrasound beam centered at a first frequency along a scan line;

transmitting a second ultrasound beam centered at a second frequency, wherein transmitting the second ultrasound beam comprises sweeping the position of the second ultrasound beam in a direction such that the second ultrasound beam intersects with the first ultrasound beam at a plurality of voxels along the scan line, wherein the second frequency is different than the first frequency;

receiving echoes associated with interaction of the first ultrasound beam and the second ultrasound beam at the plurality of voxels along the scan line; and generating an ultrasound image based on the received echoes.

2. The method of claim 1, wherein the first ultrasound beam is transmitted with a first transducer, and wherein the second ultrasound beam is transmitted with a second transducer, different than the first transducer.

3. The method of claim 2, wherein the second transducer comprises a phased array of ultrasound transducers that performs the sweeping by at least beam steering the position of the second ultrasound beam.

4. The method of claim 1, wherein the echoes associated with interaction of the first ultrasound beam and the second ultrasound beam are received with a third transducer.

5. The method of claim 4, wherein the echoes are each centered at a respective third frequency based on the first frequency of the first ultrasound beam and the respective second frequency of the second ultrasound beam.

6. The method of claim 5, wherein the third frequency corresponds to a difference between the first frequency of the first ultrasound beam and the second frequency of the second ultrasound beam.

7. The method of claim 4, wherein the third transducer is scanned during the receiving of the echoes in order to focus on the respective voxels.

8. The method of claim 7, wherein the third transducer is scanned by moving the third transducer.

9. The method of claim 7, wherein the third transducer is scanned through beam steering.

10. The method of claim 1, wherein the first ultrasound beam and the second ultrasound beam intersect at different angles, each approximately 90 degrees, at each of the plurality of voxels.

11. The method of claim 1, wherein the first ultrasound beam and the second ultrasound beam intersect at a 40 degree angle at one of the plurality of voxels.

12. The method of claim 1, wherein the first ultrasound beam and the second ultrasound beam intersect at a 140 degree angle at one of the plurality of voxels.

13. The method of claim 1, further comprising frequency modulating at least one of the first ultrasound beam and second ultrasound beam among discrete frequencies during the sweeping.

14. The method of claim 1, wherein generating the ultrasound image comprises frequency compounding.

15. The method of claim 14, wherein generating the ultrasound image further comprises spatial compounding.

* * * * *